US007048837B2

United States Patent
Somekh et al.

(10) Patent No.: US 7,048,837 B2
(45) Date of Patent: May 23, 2006

(54) END POINT DETECTION FOR SPUTTERING AND RESPUTTERING

(75) Inventors: Sasson R. Somekh, Los Altos Hills, CA (US); Marc O. Schweitzer, San Jose, CA (US); John C. Forster, San Francisco, CA (US); Zheng Xu, Foster City, CA (US); Roderick C. Mosely, Pleasanton, CA (US); Barry L. Chin, Saratoga, CA (US); Howard E. Grunes, Santa Cruz, CA (US)

(73) Assignee: Applied Materials, Inc., Santa Clara, CA (US)

( * ) Notice: Subject to any disclaimer, the term of this patent is extended or adjusted under 35 U.S.C. 154(b) by 146 days.

(21) Appl. No.: 10/659,902

(22) Filed: Sep. 11, 2003

(65) Prior Publication Data

US 2005/0173239 A1 Aug. 11, 2005

Related U.S. Application Data

(60) Provisional application No. 60/410,843, filed on Sep. 13, 2002.

(51) Int. Cl.
*C23C 14/35* (2006.01)
(52) U.S. Cl. ............... 204/192.13; 204/192.3; 204/192.33; 204/298.03; 204/298.11; 204/298.32
(58) Field of Classification Search ........... 204/192.13, 204/192.3, 192.33, 298.11, 298.03, 298.32
See application file for complete search history.

(56) References Cited

U.S. PATENT DOCUMENTS 3,664,942 A * 5/1972 Havas et al. ........... 204/192.33

| | | | |
|---|---|---|---|
| 5,160,576 A | 11/1992 | Robbins | 216/60 |
| 5,290,383 A | 3/1994 | Koshimizu | 156/345.25 |
| 5,347,460 A | 9/1994 | Gifford et al. | 700/121 |

(Continued)

OTHER PUBLICATIONS

Radzimski, Z. J., et al. "Optical emission spectroscopy of high density metal plasma formed during magnetron sputtering." J. Vac. Sci. Tech., B 15(2), Mar./Apr. 1997; pp 202-208.

*Primary Examiner*—Rodney G. McDonald
(74) *Attorney, Agent, or Firm*—Konrad, Raynes & Victor, LLP

(57) ABSTRACT

Plasma etching or resputtering of a layer of sputtered materials including opaque metal conductor materials may be controlled in a sputter reactor system. In one embodiment, resputtering of a sputter deposited layer is performed after material has been sputtered deposited and while additional material is being sputter deposited onto a substrate. A path positioned within a chamber of the system directs light or other radiation emitted by the plasma to a chamber window or other optical view-port which is protected by a shield against deposition by the conductor material. In one embodiment, the radiation path is folded to reflect plasma light around the chamber shield and through the window to a detector positioned outside the chamber window. Although deposition material may be deposited onto portions of the folded radiation path, in many applications, the deposition material will be sufficiently reflective to permit the emission spectra to be detected by a spectrometer or other suitable detector without significant signal loss. The etching or resputtering may be terminated when the detector detects that an underlying layer has been reached or when some other suitable process point has been reached.

26 Claims, 9 Drawing Sheets

U.S. PATENT DOCUMENTS

| | | | |
|---|---|---|---|
| 5,728,253 A | 3/1998 | Saito et al. | 156/345.25 |
| 5,871,658 A | 2/1999 | Tao et al. | 216/60 |
| 5,980,767 A | 11/1999 | Koshimizu et al. | 216/60 |
| 6,117,348 A | 9/2000 | Peng et al. | 216/60 |
| 6,121,147 A | 9/2000 | Daniel et al. | 438/692 |
| 6,190,927 B1 | 2/2001 | Liu | 438/8 |
| 6,207,008 B1 | 3/2001 | Kijima | 216/59 |
| 6,258,497 B1 | 7/2001 | Kropp et al. | 430/30 |
| 6,265,316 B1 | 7/2001 | Yoshida | 438/700 |
| 6,297,064 B1 | 10/2001 | Koshimizu | 438/9 |
| 6,326,794 B1 | 12/2001 | Lundquist et al. | 324/678 |
| 6,813,534 B1 * | 11/2004 | Sui et al. | 700/121 |
| 2001/0007772 A1 | 7/2001 | Li et al. | |

* cited by examiner

END POINT DETECTION FOR SPUTTERING AND RESPUTTERING

RELATED APPLICATIONS

This application claims the benefit of the U.S. Provisional Application No. 60/410,843 filed Sep. 13, 2002, which is incorporated by reference in entirety.

FIELD OF THE INVENTION

The inventions relate generally to sputtering and resputtering. In particular, the inventions relate to the sputter deposition of material and resputtering of deposited material in the formation of semiconductor integrated circuits.

BACKGROUND ART

Semiconductor integrated circuits typically include multiple levels of metallization to provide electrical connections between large numbers of active semiconductor devices. Advanced integrated circuits, particularly those for microprocessors, may include five or more metallization levels. In the past, aluminum has been the favored metallization, but copper has been developed as a metallization for advanced integrated circuits.

A typical metallization level is illustrated in the cross-sectional view of FIG. 1. A lower-level layer 110 includes a conductive feature 112. If the lower-level layer 110 is a lower-level dielectric layer, such as silica or other insulating material, the conductive feature 112 may be a lower-level copper metallization, and the vertical portion of the upper-level metallization formed in a hole is referred to as a via since it interconnects two levels of metallization. If the lower-level layer 110 is a silicon layer, the conductive feature 112 may be a doped silicon region, and the vertical portion of the upper-level metallization is referred to as a contact because it electrically contacts silicon. An upper-level dielectric layer 114 is deposited over the lower-level dielectric layer 110 and the lower-level metallization 112. There are yet other shapes for the holes including lines and trenches. Also, in dual damascene and similar interconnect structures, as described below, the holes have a complex shape. In some applications, the hole may not extend through the dielectric layer. The following discussion will refer only to via holes, but in most circumstances the discussion applies equally well to other types of holes with only a few modifications well known in the art.

Conventionally, the dielectric layer is silicon oxide formed by plasma-enhanced chemical vapor deposition (PECVD) using tetraethylorthosilicate (TEOS) as the precursor. However, low-k materials of other compositions and deposition techniques are being considered. Some of the low-k dielectrics being developed can be characterized as silicates, such as fluorinated silicate glasses. Hereafter, only silicate (oxide) dielectrics will be directly described, but it is contemplated that other dielectric compositions may be used.

A via hole is etched into the upper-level dielectric layer 114 typically using, in the case of silicate dielectrics, a fluorine-based plasma etching process. In advanced integrated circuits, the via holes may have widths as low as 0.18 µm or even less. The thickness of the dielectric layer 114 is usually at least 0.7 µm, and sometimes twice this, so that the aspect ratio of the hole may be 4:1 or greater. Aspect ratios of 6:1 and greater are being proposed. Furthermore, in many circumstances, the via hole often has a vertical profile.

A liner layer 116 may be deposited onto the bottom and sides of the hole and above the dielectric layer 114. The liner 116 can perform several functions. It can act as an adhesion layer between the dielectric and the metal since metal films tend to peel from oxides. It can also act as a barrier against inter-diffusion between the oxide-based dielectric and the metal. It may also act as a seed and nucleation layer to promote the uniform adhesion and growth and possibly low-temperature reflow for the deposition of metal filling the hole and to nucleate the even growth of a separate seed layer. One or more liner layers may be deposited, in which one layer may function primarily as a barrier layer and others may function primarily as adhesion, seed or nucleation layers.

An interconnect layer 118 of a conductive metal such as copper, for example, is then deposited over the liner layer 116 to fill the hole and to cover the top of the dielectric layer 114. Conventional aluminum metallizations are patterned into horizontal interconnects by selective etching of the planar portion of the metal layer 118. However, a preferred technique for copper metallization, called dual damascene, forms the hole in the dielectric layer 114 into two connected portions, the first being narrow vias through the bottom portion of the dielectric and the second being wider trenches in the surface portion which interconnect the vias. After the metal deposition, chemical mechanical polishing (CMP) is performed which removes the relatively soft copper exposed above the dielectric oxide but which stops on the harder oxide. As a result, multiple copper-filled trenches of the upper level, similar to the conductive feature 112 of the next lower level, are isolated from each other. The copper-filled trenches act as horizontal interconnects between the copper-filled vias. The combination of dual damascene and CMP eliminates the need to etch copper. Several layer structures and etching sequences have been developed for dual damascene, and other metallization structures have similar fabrication requirements.

Lining and filling via holes and similar high aspect-ratio structures, such as occur in dual damascene, have presented a continuing challenge as their aspect ratios continue to increase. Aspect ratios of 4:1 are common and the value will further increase. An aspect ratio as used herein is defined as the ratio of the depth of the hole to narrowest width of the hole, usually near its top surface. Via widths of 0.18 µm are also common and the value will further decrease. For advanced copper interconnects formed in oxide dielectrics, the formation of the barrier layer tends to be distinctly separate from the nucleation and seed layer. The diffusion barrier may be formed from a bilayer of Ta/TaN, W/WN, or Ti/TiN, or of other structures. Barrier thicknesses of 10 to 50 nm are typical. For copper interconnects, it has been found useful to deposit one or more copper layers to fulfill the nucleation and seed functions.

The deposition of the liner layer or the metallization by conventional physical vapor deposition (PVD), also called sputtering, is relatively fast. A DC magnetron sputtering reactor system has a target composed of the metal to be sputter deposited and which is powered by a DC electrical source. The magnetron is scanned about the back of the target and projects its magnetic field into the portion of the reactor system adjacent the target to increase the plasma density there to thereby increase the sputtering rate. However, conventional DC sputtering (which will be referred to as PVD in contrast to other types of sputtering to be introduced) predominantly sputters neutral atoms. The typical ion densities in PVD are often less than $10^9$ cm$^{-3}$. PVD also tends to sputter atoms into a wide angular distribution, typically having a cosine dependence about the target normal. Such a wide distribution can be disadvantageous for filling a deep and narrow via hole 122 such as that illustrated in FIG. 2, in which a barrier layer 124 has already been deposited. The large number of off-angle sputter particles can cause a layer 126 to preferentially deposit around the upper corners of the hole 122 and form overhangs 128. Large overhangs can further restrict entry into the hole 122 and cause inadequate coverage of the sidewalls 130 and bottom 132 of the hole 122. Also, the overhangs 128 can bridge the hole 122 before it is filled and create a void 134 in the metallization within the hole 122. Once a void 134 has formed, it is often difficult to reflow it out by heating the metallization to near its melting point. Even a small void can introduce reliability problems. If a second metallization deposition step is planned, such as by electroplating, the bridged overhang makes subsequent deposition more difficult.

One approach to ameliorate the overhang problem is long-throw sputtering, in which the sputtering target is spaced relatively far from the wafer or other substrate being sputter coated. For example, the target-to-wafer spacing can be at least 50% of the wafer diameter, preferably more than 90%, and more preferably more than 140%. As a result, the off-angle portion of the sputtering distribution is preferentially directed to the chamber walls, but the central-angle portion remains directed substantially to the wafer. The truncated angular distribution can cause a higher fraction of the sputter particles to be directed deeply into the hole 122 and reduce the extent of the overhangs 128. A similar effect can be accomplished by positioning a collimator between the target and wafer. Because the collimator has a large number of holes of high aspect ratio, the off-angle sputter particles tend to strike the sidewalls of the collimator, and the central-angle particles tend to pass through.

Another technique for deep hole lining and filling is sputtering using a PVD sputtering process called ionized metal plasma (IMP). A typical high-density plasma is one having an average plasma density across the plasma, exclusive of the plasma sheaths, of at least $10^{11}$ cm$^3$, and preferably at least $10^{12}$ cm$^{-3}$. In IMP deposition, a separate plasma source region is formed in a region away from the wafer, for example, by inductively coupling RF power into a plasma from an electrical coil wrapped around a plasma source region between the target and the wafer. The plasma generated in this fashion is referred to as an inductively coupled plasma (ICP). An IMP chamber having this configuration is commercially available from Applied Materials of Santa Clara, Calif. Other IMP sputter reactor systems are available. The higher power ionizes not only the argon working gas, but also significantly increases the ionization fraction of the sputtered atoms, that is, produces metal ions. The wafer either self-charges to a negative potential or is RF biased to control its DC potential. The metal ions are accelerated across the plasma sheath as they approach the negatively biased wafer. As a result, their angular distribution becomes strongly peaked in the forward direction so that they are drawn deeply into the via hole. Overhangs become much less of a problem in IMP sputtering, and bottom coverage and bottom sidewall coverage are relatively high.

Another technique for depositing metals is sustained self-sputtering (SSS). Examples are described by Fu et al. in U.S. Pat. No. 6,692.617 issued Feb. 17, 2004 and by Fu in U.S. Pat. No. 6,183,614 B1 issued Feb. 6, 2001. For example, at a sufficiently high plasma density adjacent a copper target, a sufficiently high density of copper ions develops that the copper ions will resputter the copper target with yield over unity. The supply of argon working gas can then be eliminated or at least reduced to a very low pressure while the copper plasma persists. Aluminum is believed to be not readily susceptible to SSS. Some other materials, such as Pd, Pt, Ag, and Au can also undergo SSS.

Techniques and reactor structures have been developed to promote sustained self-sputtering. It has been observed that some sputter materials not subject to SSS because of sub-unity resputter yields nonetheless benefit from these same techniques and structures, presumably because of partial self-sputtering, which results in a partial self-ionized plasma (SIP). Furthermore, it is often advantageous to sputter copper with a low but finite argon pressure even though SSS without any argon working gas is achievable. Hence, SIP sputtering is the preferred terminology for the more generic sputtering process involving a reduced or zero pressure of working gas so that SSS is a type of SIP.

In the formation of semiconductor devices, it is often useful to remove a deposited layer or a portion of a layer. Plasmas may be employed in etch processes to provide ions to facilitate the removal of material from a semiconductor workpiece. In some processes, the ions may react chemically with a layer on the workpiece. In other processes, the ions may strike the workpiece with sufficient force to sputter material from the workpiece.

The etch process is often performed in a separate etch chamber designed for that purpose. The progress of the etch process may be monitored to determine an endpoint at which the etch process should be terminated. For example, in etching a first material disposed on a second material, it is often useful to terminate the etching process once the first material has been etched away sufficiently to expose the underlying second material. One known method for monitoring plasma etching is to monitor the light emitted by the plasma. Chemical constituents in the plasma such as reactant species or plasma etch products can be excited by the plasma. As the excited atoms decay, they will emit light having wavelengths which are characteristic of the atoms. The light or other radiation emitted by the plasma may be monitored through a chamber window by an appropriate detector positioned outside the chamber window. By monitoring the intensity of the plasma emissions at the wavelength or wavelengths characteristic of particular species in the plasma, the concentration of those species in the plasma can be determined. These concentrations can in turn be used to indicate the progress of the plasma etch which can then be terminated at the appropriate point.

SUMMARIES OF ILLUSTRATIVE EMBODIMENTS

Plasma etching or resputtering of a layer of sputtered materials including opaque metal conductor materials may be controlled in a sputter reactor system. In one embodiment, resputtering of a sputter deposited layer is performed while additional material is being sputter deposited onto a substrate. A path positioned within a chamber of the system directs light or other radiation emitted by the plasma to a chamber window or other optical view-port which is protected by a shield against deposition by the conductor material. In one embodiment, the radiation path is folded to reflect plasma light around the chamber shield and through the window to a detector positioned outside the chamber window.

In some applications, the chamber shield may be positioned to inhibit the deposition of conductor material or other opaque sputtered material onto the window, thereby permitting the deposition of material onto the substrate in a prior step or at the same time that material is being resputtered or etched from the substrate. Although deposition material may be deposited onto portions of the folded radiation path, in many applications, the deposition material will be sufficiently reflective to permit the emission spectra to be detected by a spectrometer or other suitable detector without significant signal loss. The etching or resputtering may be terminated when the detector detects that an underlying layer has been reached or when some other suitable process point has been reached.

The end point detection systems and methods of the present inventions may be used in a variety of chambers including sputtering chambers. One embodiment of the present inventions is directed to sputter depositing a liner material, such as tantalum or tantalum nitride, by combining long-throw sputtering, self-ionized plasma (SIP) sputtering, inductively-coupled plasma (ICP) resputtering, and coil sputtering in one chamber. Long-throw sputtering is characterized by a relatively high ratio of the target-to-substrate distance and the substrate diameter. SIP, particularly at low pressures (for example, below 5 mTorr), tends to be promoted by magnetrons having relatively small areas to thereby increase the target power density, and by magnetrons having asymmetric magnets causing the magnetic field to penetrate farther toward the substrate. Long-throw SIP sputtering promotes deep hole coating of both the ionized and neutral deposition material components.

ICP resputtering can reduce the thickness of layer bottom coverage of deep holes to reduce contact resistance. During ICP resputtering, ICP coil sputtering can deposit a protective layer, particularly on areas such as adjacent the hole openings where thinning by resputtering may not be desired. During the ICP resputtering, the emissions of the plasma may be monitored through a folded radiation path to a detector positioned either outside a chamber window or within the chamber pressure walls but protected from sputter deposition by a suitable shield. Once the appropriate emissions have been detected, the ICP resputtering may be terminated.

In one embodiment, the folded radiation path includes an optical array of reflective surfaces positioned to reflect radiation emitted from the plasma, either directly to a protected detector or through a chamber window to an outside detector. In one embodiment, the optical array forms a labyrinth which blocks or inhibits transmission of sputtered material through the array. The chamber shield may have an opening aligned with one end of the labyrinth to admit radiation emitted from the plasma to the labyrinth. The labyrinth has a plurality of angled paths which reflect the plasma radiation from one end of the labyrinth to the other while inhibiting the passage of sputtered deposition material through the labyrinth. Sputtered deposition material may be further confined within the labyrinth by a conduit having a plurality of portions which are not aligned with respect to each other to inhibit the passage of deposition material from one conduit portion to the next.

It should be understood that the preceding is merely a brief summary of some embodiments and aspects of the present inventions. Additional embodiments and aspects of the present inventions are referenced below. It should further be understood that numerous changes to the disclosed embodiments can be made without departing from the spirit or scope of the inventions. The preceding summary therefore is not meant to limit the scope of the inventions. Rather, the scope of the inventions is to be determined only by the appended claims and their equivalents.

DESCRIPTIONS OF ILLUSTRATIVE EMBODIMENTS

Plasma etching or resputtering of a variety of materials such as opaque metal conductor materials may be controlled in a reactor system such as a sputter reactor system. An example of such a reactor system is illustrated generally at 138 in FIGS. 3 and 6. In this reactor system, selected aspects of both SIP and ICP plasma generation techniques, are utilized, either in separate steps or at the same time in a reactor chamber 140 in a manner similar to that described in copending application Ser. No. 10/202,778, now abandoned. For example, an SIP film may be sputter deposited into a high-aspect ratio via. In addition, bottom coverage may be thinned or eliminated by ICP resputtering of the bottom of the via while upper portions of a liner layer sidewall may be protected from resputtering by sputtering an ICP coil 141 located within the chamber 140 to deposit coil material onto the substrate. Resputtering of the layer bottom may be ended when the layer bottom is sufficiently thinned such that atoms of the underlying layer are exposed and sputtered. These underlying layer atoms may be detected within the plasma by a detector 142 which detects the light emitted by the underlying layer material atoms through a folded radiation path 143.

Figure 4:
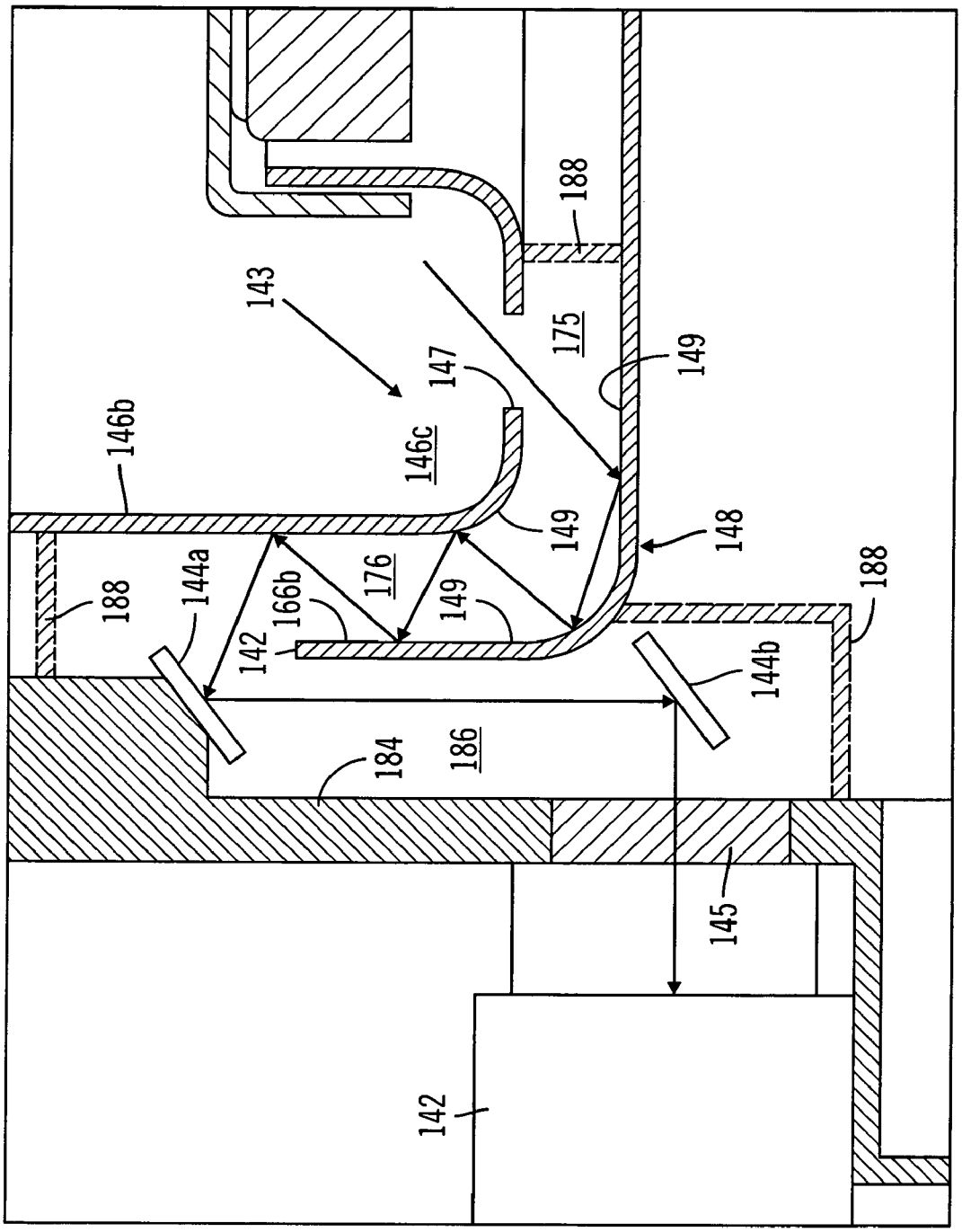
FIG. 4 is a schematic cross-sectional diagram of a folded radiation path of the chamber of FIG. 3.

As best seen in FIG. 4, the folded radiation path 143 of the illustrated embodiment includes a pair of mirrors 144a, 144b of an optical array positioned to reflect light emitted from the plasma to the detector 142 through a chamber window 145 which is an optical view-port in a pressure wall of the chamber. A shield 146 protects the chamber interior including the window 145 from the deposition of sputtered material. One or more orifices 147 in the shield 146 permit the plasma glow to pass from the chamber plasma area to the folded radiation path 143.

The optical array of the folded radiation path 143 further includes a labyrinthine structure 148 to inhibit the passage of sputtered material through the folded radiation path and any subsequent deposition of the material onto the chamber window 145. The labyrinth 148 has a plurality of reflective interior surfaces 149 to reflect the light through the labyrinth. In this manner, the plasma glow may be reflected in a folded path from the plasma to the detector 142 through the window 145 while reducing or eliminating the deposition of sputtered material onto the chamber window 145. Deposition of sputtered material onto the internal reflective surfaces 149 of the labyrinth 148 may not significantly reduce reflection by the surfaces 144, particularly where the sputtered material is a reflective material such as a conductor material.

The reactor system 138 (FIG. 3) of the illustrated embodiment is a DC magnetron type reactor system based on a modification of the Endura PVD Reactor available from Applied Materials, Inc. of Santa Clara, Calif. The chamber 140 of the reactor system 138 is a vacuum chamber usually made of metal and electrically grounded, sealed through a target isolator 154 to a PVD target 156 having at least a surface portion 157 composed of the material to be sputter deposited on a wafer 158. The wafer may be different sizes including 150, 200, 300 and 450 mm. The illustrated reactor system 138 can generate a plasma within the chamber 140 by self ionization and by inductive coupling. In one embodiment, the self ionized plasma may be used to perform self-ionized sputtering (SIP) in a long-throw mode. This SIP mode may be used for example when nonuniform coverage is desired, such as coverage primarily directed to the sidewalls of the hole. The SIP mode may be used to achieve more uniform coverage also.

The chamber 140 also has the RF coil 141 which inductively couples RF energy into the interior of the chamber. The RF energy provided by the coil 141 ionizes a precursor gas such as argon to maintain a plasma to resputter a deposition layer using ionized argon to thin bottom coverage, or to ionize sputtered deposition material to improve bottom coverage. Thus, the plasma may be used to resputter a deposited layer or to ionize sputtered deposition material, or both.

Still further, the coil 141 itself may be sputtered to provide a protective coating on the wafer during resputtering of the material deposited onto the wafer for those areas in which thinning of the deposited material is not desired, or to otherwise provide additional deposition material. Thus, the reactor system 138 of the illustrated embodiment, has two targets, a first target 156 facing the substrate and a second target, the coil 141, which surrounds the plasma generation area between the first target 156 and the substrate.

Although the plasma used to resputter the deposited material in the chamber 140 of the illustrated embodiment is maintained by RF energy inductively coupled from the RF coil 141 in the illustrated embodiment, it is recognized that an endpoint detection system in accordance with the present invention may be used in other types of chambers. For example, an etching plasma may be maintained in a sputtering chamber by energy supplied by capacitively coupled electrodes such as a target and a pedestal electrode.

In the illustrated embodiment, the shield 146 surrounds the plasma generation area and protects the window 145 from the deposition of material sputtered from the target 156 and the coil 141. These deposition materials are often relatively opaque such that if deposited on the chamber window 145 to an appreciable degree, the transmission of light or other radiation to the detector could be substantially inhibited. The shield 146 permits sputter deposition to be performed in the chamber, yet coating of the window 145 is substantially reduced or eliminated. Furthermore, the folded radiation path 143 conducts the light and other radiation emitted from the plasma, around the shield 146, and to the chamber window 145 and the detector 142 positioned on the exterior of the window 145. In this manner, the folded radiation path 143 permits the detector 142 to monitor the radiation emitted by the plasma during an etching operation while the shield 146 protects the chamber window 145 from the material being deposited onto the substrate.

In addition to protecting the chamber interior walls, the shield 146 has an upper portion 146a (FIG. 7) spaced from the peripheral edge 157a of the sputtering surface 157 of the target 156. The shield upper portion 146a functions as a darkspace shield.

The chamber 140 also has an outer shield 166 which substantially surrounds the inner shield 146. The inner and outer shields 146 and 166 separated by a second dielectric shield isolator 168 are held within the chamber 140 to protect the chamber wall 140 including the chamber window 145 from the sputtered material. In the illustrated embodiment, both the inner and outer shields 146 and 166 are grounded. However, in some embodiments, one or both shields may be floating or biased to a nonground level. The inner shield 146 can also act as an anode grounding plane in opposition to the cathode target 156, thereby capacitively supporting a plasma. If the darkspace shield is permitted to float electrically, some electrons can deposit on the darkspace shield 146 so that a negative charge builds up there. It is believed that the negative potential could not only repel further electrons from being deposited, but also confine the electrons in the main plasma area, thus reducing the electron loss, sustaining low-pressure sputtering, and increasing the plasma density, if desired.

The coil 141 is carried on the shield 146 by a plurality of coil standoffs 170 which electrically insulate the coil 141 from the supporting shield 146 which is typically at a different potential. To enable use of the coil as a circuit path, RF power is passed through the vacuum chamber walls and through the shield 146 to ends of the coil 141. Vacuum feedthroughs (not shown) extend through the vacuum chamber wall to provide RF current from a generator preferably located outside the vacuum pressure chamber. RF power is applied through the shield 146 to the coil 141 by feedthrough standoffs 172, which like the coil standoffs 170, have labyrinthine passageways to prevent formation of a path of deposited material from the coil 141 to the shield 146 which could short the coil 141 to the shield 146.

The inner shield 146 is generally bowl-shaped and includes a generally cylindrically shaped, vertically oriented side wall 146b to which the standoffs 170 and 172 are attached to insulatively support the coil 141. The inner shield further has a generally annular shaped bottom wall 146c which defines a central opening through which the pedestal 162 extends. The outer shield 166 is similarly generally bowl-shaped and includes a generally cylindrically shaped, vertically oriented side wall 166b and a generally annular shaped bottom wall 166c which defines a central opening through which the pedestal 162 extends.

As best seen in FIG. 4, a portion of the spaced inner and outer shields 146 and 166 form the labyrinth 148 of the folded radiation path 143. As previously mentioned, the labyrinth 148 optically couples the conductance orifice 147 in the inner shield 146 to the mirrors 144a and 144b of the folded radiation path 143 such that light or other radiation emitted by the plasma through the shield orifice 147 is reflected by the interior surfaces 149 of the labyrinth to the mirrors 144a, 144b which reflect the radiation through the chamber window 145 to the detector 142.

The labyrinth 148 comprises a conduit having two non-aligned portions 175 and 176. The first conduit portion 175 is formed by the spaced bottom walls 146*c* and 166*c* of the inner and outer shields 146 and 166, respectively. Radiation emitted by the plasma enters the first conduit 175 through the inner shield orifice 147 of the first conduit 175.

The second conduit portion 176 is formed by the spaced side walls 146*b* and 166*b* of the inner and outer shields 146 and 166, respectively. Radiation entering the first conduit portion 175 from the plasma is reflected by the interior surfaces of the conduit portion 175 to the interior surfaces of the conduit portion 176 which in turn reflect the radiation to the chamber mirror 144*a* through an aperture 182 in the outer shield 166. As previously mentioned, the reflective surfaces of the mirrors 144*a* and 144*b* reflect the plasma radiation to the detector 142 which detects the wavelengths of the plasma radiation to determine an appropriate end point of the etching operation.

As shown in FIG. 4, the conduit portions 175 and 176 are orthogonal with respect to each other rather than being coaxially aligned. As a consequence, sputtered deposition material which enters the inner shield orifice 147 deposits primarily on interior surfaces of the first conduit portion 175 and to a substantially lesser extent on the interior surfaces of the second conduit portion 176. In one embodiment, the sputtered material is a metal or metal compound which is relatively reflective such that deposited deposition material in the interior of the folded radiation path does not prevent the reflection of radiation to the detector.

The chamber wall portion 184 supporting the mirrors 144*a* and 144*b*, together with the outer surface of the outer shield 166, forms a third conduit portion 186 through which the mirrors 144*a* and 144*b* reflect the plasma radiation to the chamber window 145 disposed in the chamber exterior wall. The third conduit portion 186 is also not coaxially aligned with respect to the second conduit portion but is instead parallel to the second conduit portion. As a consequence, any sputtered deposition material which exits the second conduit portion orifice 182 deposits primarily on interior surfaces of the third conduit portion 186 adjacent to the orifice 182 rather than on the chamber window 145. In this manner, the shields 146 and 166 and the folded radiation path inhibit the deposition of sputtered material onto the chamber window 145, yet reflect the plasma radiation from the plasma through the window 145 and to the detector 142.

In the illustrated embodiments, the conduit portions 175, 176 and 186 are shown as being orthogonal or parallel with respect to each other. It is appreciated that portions of a folded radiation path may be oriented at other angles to inhibit or otherwise reduce the transmission of sputtered material through the radiation path yet permit radiation to be reflected through the path.

Figure 3:
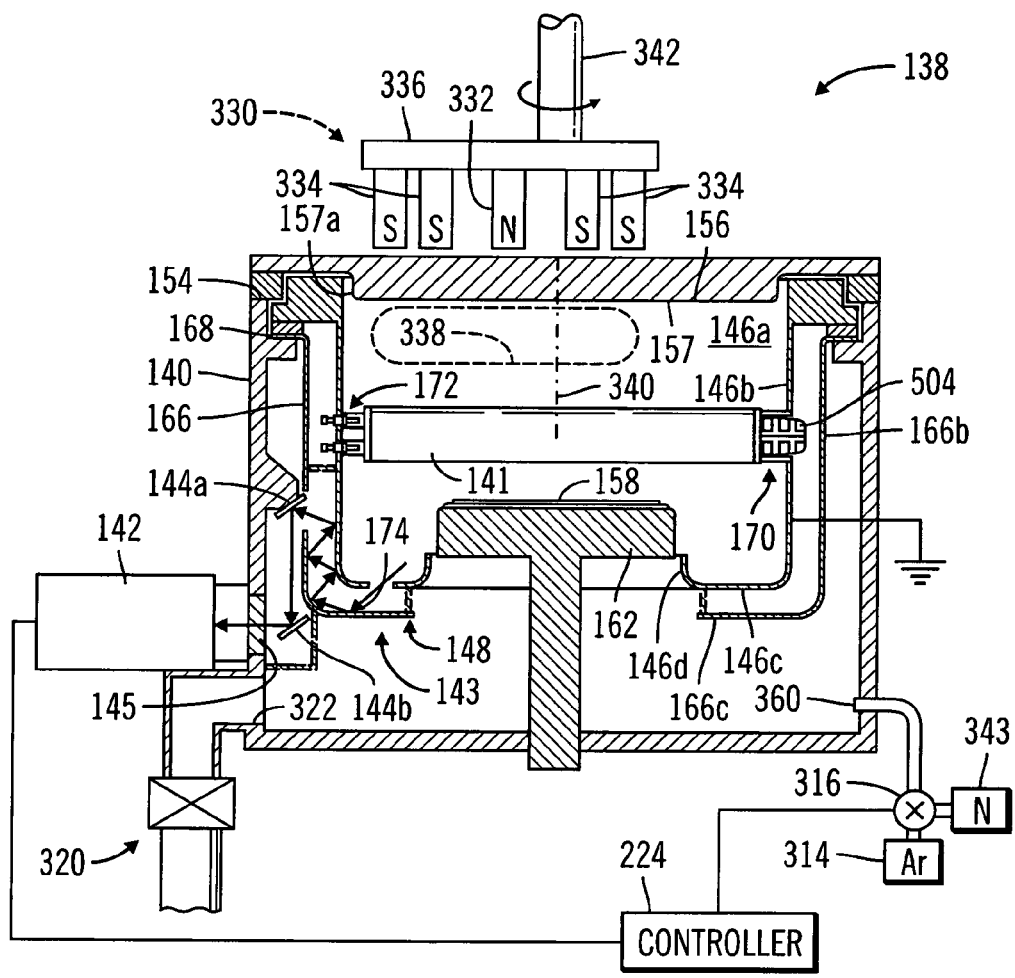
FIG. 3 is a schematic representation of a sputtering chamber usable with an embodiment of the invention.
Figure 5:
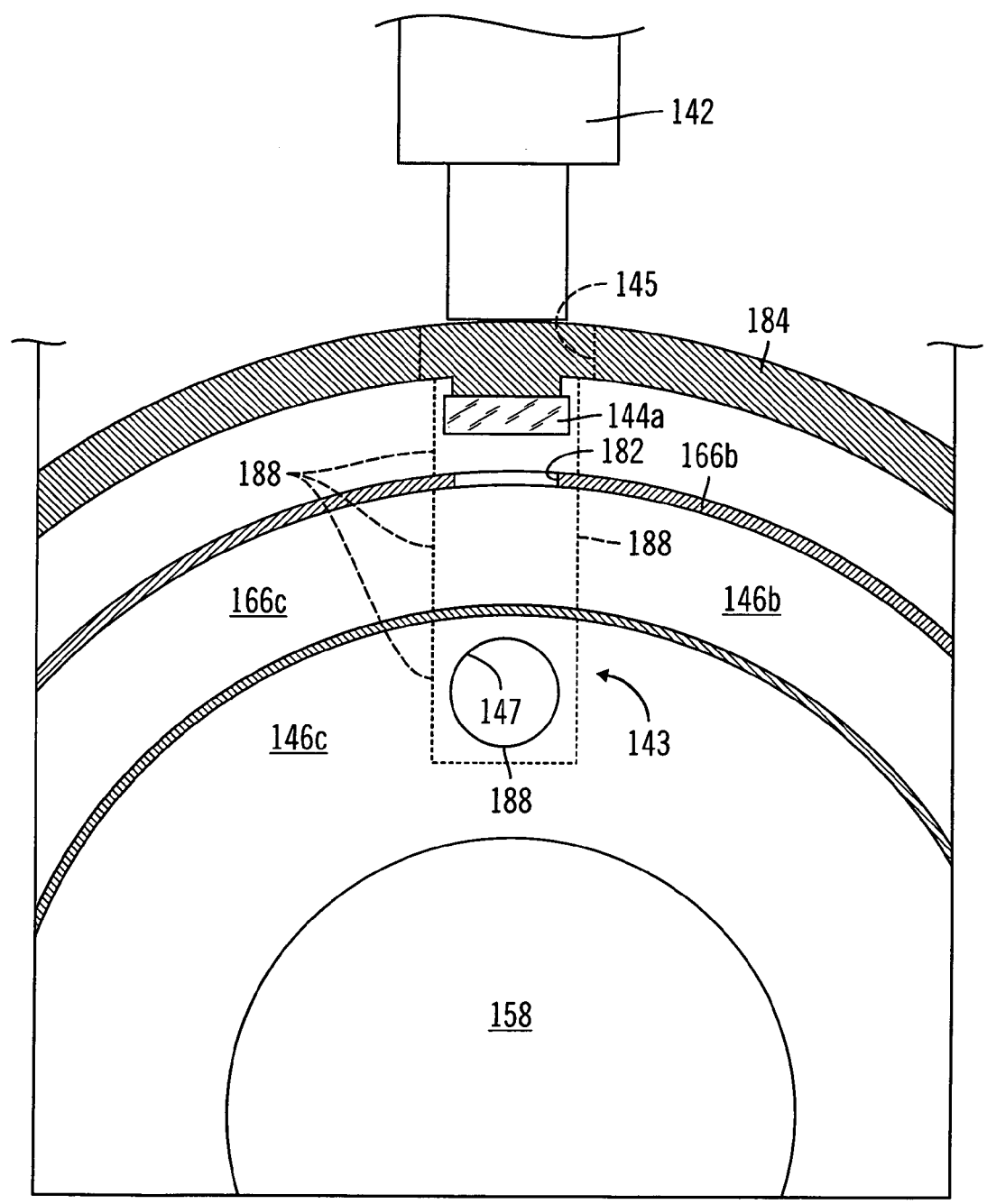
FIG. 5 is a schematic top view of the folded radiation path of FIG. 4.

To further restrict the deposition of sputtered material entering the shield orifice 146, the folded light path 143 may include sidewalls 188 disposed around the orifice 146 between the shields 146 and 166 as indicated in phantom in FIGS. 3–5. The sidewalls 188 may further enclose the conduit portions 175, 176 or 186 of the folded light path 143 to prevent sputtered material from depositing on chamber surfaces outside the folded light path 143.

Figure 6:
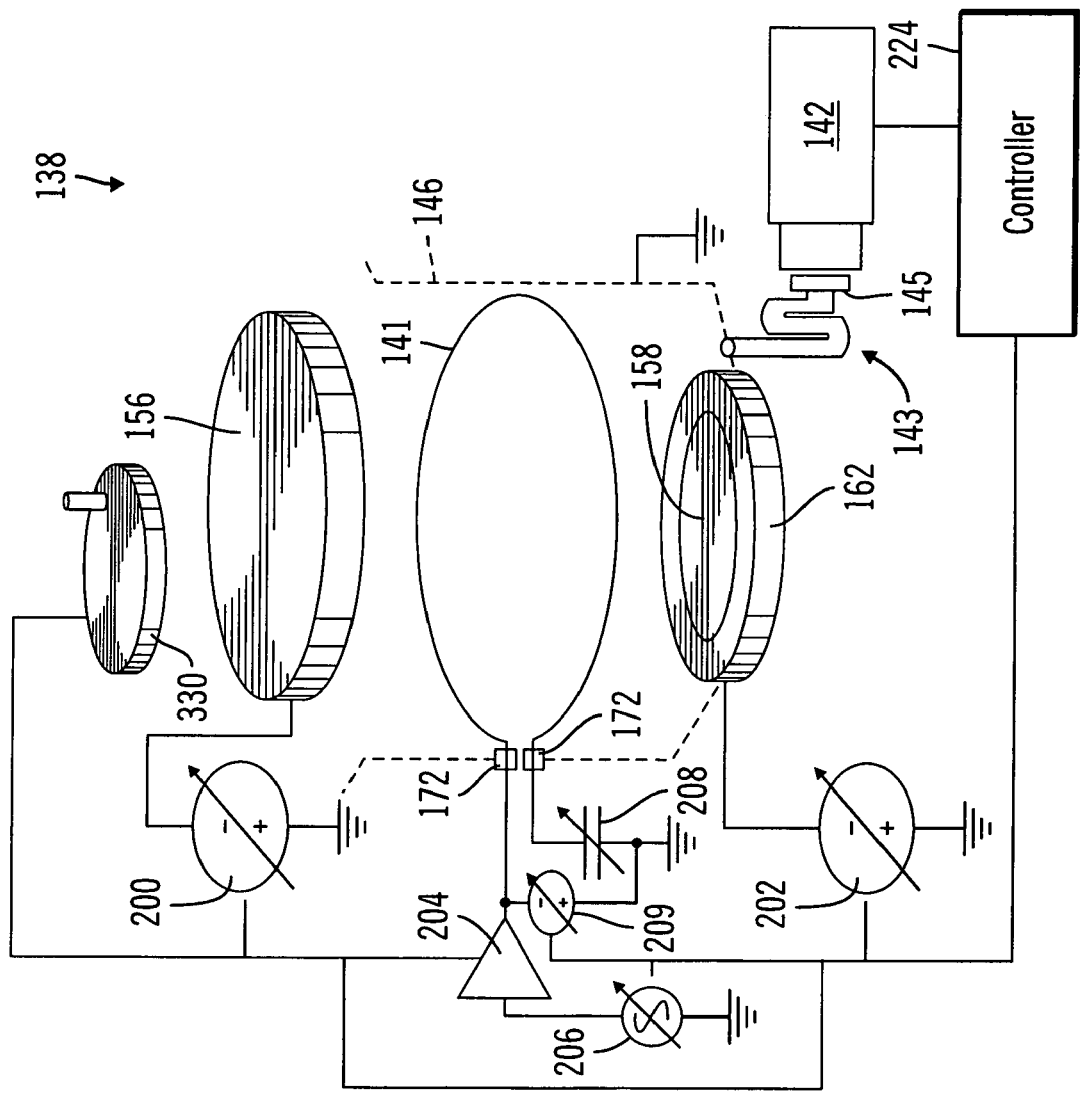
FIG. 6 is a schematic representation of electrical interconnections of various components of the sputtering chamber of FIG. 3.

FIG. 6 is a schematic representation of the electrical connections of the plasma generating apparatus of the illustrated embodiment. To attract the ions generated by the plasma, the target 156 is preferably negatively biased by a variable DC power source 200 at a DC power of 1–40 kW, for example. The source 200 negatively biases the target 156 to about −400 to −600 VDC with respect to the chamber shield 166 to ignite and maintain the plasma. A target power of between 1 and 5 kW is typically used to ignite the plasma while a power of greater than 10 kW is preferred for the SIP sputtering described here. For example, a target power of 24 kW may be used to deposit tantalum nitride by SIP sputtering and a target power of 20 kW may be used to deposit tantalum by SIP sputtering. During ICP resputtering the target power may be reduced to 100–200 watts, for example to maintain plasma uniformity. Alternatively, the target power may be maintained at a high level if target sputtering during ICP resputtering is desired, or may be turned off entirely, if desired.

The pedestal 162 and hence the wafer 158 may be left electrically floating, but a negative DC self-bias may nonetheless develop on it. Alternatively, the pedestal 162 may be negatively biased by a source 202.

One end of the coil 141 is insulatively coupled through the shield 166 by a feedthrough standoff 172 to an RF source such as the output of an amplifier and matching network 204. The input of the matching network 204 is coupled to an RF generator 206, which provides RF power at approximately 1 to 3 kW watts for ICP plasma generation for this embodiment. For example, a power of 1.5 kW for tantalum nitride deposition and a power of 1 kW for tantalum deposition may be used. A range of 50 watts to 10 kW may also be used. During SIP deposition, the RF power to the coil may be turned off if desired. Alternatively, RF power may be supplied during SIP deposition if desired.

The other end of the coil 141 is also insulatively coupled through the shield 166 by a similar feedthrough standoff 172 to ground, for example through a blocking capacitor 208 which may be a variable capacitor, to provide a DC bias on the coil 141. The DC bias on the coil 141 may be controlled through a DC power source 209 coupled to the coil 141. The sputtering of the coil 141 to deposit coil material onto the substrate may be controlled by controlling the DC bias on the coil. Suitable DC power ranges for ICP plasma generation and coil sputtering include 50 watts to 10 kWatts. One example is 500 watts during coil sputtering. DC power to the coil 141 may be turned off during SIP deposition, if desired.

The above-mentioned power levels may vary of course, depending upon the particular application. A computer-based controller 224 may be programmed to control the power levels, voltages, currents and frequencies of the various sources in accordance with the particular application. Still further, the controller 224 may be programmed to respond to the detector 142 to terminate the resputtering of the substrate when the deposited layer bottom is sufficiently thinned. For example, resputtering may be terminated when atoms of the underlying layer are exposed and sputtered. These underlying layer atoms may be detected within the plasma through the folded radiation path 143 by the detector 142 by detecting the light emitted by the underlying layer material atoms when they become dispersed in the plasma through the resputtering action. Thus, for example, if tantalum is being deposited on an underlying layer of copper, resputtering to thin a portion of the tantalum layer may be terminated when the emission spectra of copper atoms is detected. The controller 224 can reduce or terminate the resputtering process by controlling the RF power supplied to the ICP coil 141 by the RF power supply 206.

The emission lines of copper atoms have been tabulated, for example, in the CRC Handbook of Chemistry and Physics. The actual spectrum of copper atoms in a magnetron plasma has been published by Radzimski, Hankins, Cuomo, Posadowksi and Shingubara, J. Vac. Sci. Tech. B15, pp 202–208. This paper indicates that emission lines at 402 nm, 510 nm and 793 nm would be suitable candidates for endpoint detection. Thus, for detecting copper atoms, an optical emission spectroscopy system sensitive to these emission spectra would be suitable for the detector 142. Also, a spectrometer or optical multichannel analyzer assembly, or equivalent optical device, that has a resolution of at least 5 A, for example, over the range of 390–440 A, for example, or 710–810 A, for example, may suffice. For example, a EG&G Model 1460 optical multichannel analyzer coupled with a Jarrel-Ash Monospec 27 spectrometer with a 600 groove/mm grating may suffice.

The controller 224 may be a programmed general purpose computer such as a personal computer or a workstation such as those manufactured by Sun Microsystems, Inc. In other embodiments, dedicated purpose controllers may be used.

The RF coil 141 may be positioned relatively low in the chamber so that material sputtered from the coil has a low angle of incidence when striking the wafer. As a consequence, coil material may be deposited preferentially on the upper corners of the holes so as to protect those portions of the hole when the hole bottoms are being resputtered by the ICP plasma. In the illustrated embodiment, the coil is positioned closer to the wafer than to the target when the primary function of the coil is to generate a plasma to resputter the wafer and to provide the protective coating during resputtering. For many applications, it is believed that a coil to wafer spacing of 0 to 500 mm will be appropriate. It is appreciated however that the actual position will vary, depending upon the particular application. In those applications in which the primary function of the coil is to generate a plasma to ionize deposition material, the coil may be positioned closer to the target. Also, as set forth in greater detail in U.S. Pat. No. 6,368,469 entitled "Coils for Generating a Plasma and for Sputtering," issued Apr. 9, 2002 and assigned to the assignee of the present application, an RF coil may also be positioned to improve the uniformity of the deposited layer with sputtered coil material. In addition, the coil may have a plurality of turns formed in a helix or spiral or may have as few turns as a single turn to reduce complexity and costs and facilitate cleaning.

A variety of coil support standoffs and feedthrough standoffs may be used to insulatively support the coils. Since sputtering, particularly at the high power levels associated with SSS, SIP and ICP, involves high voltages, dielectric isolators typically separate the differently biased parts. As a result, it is desired to protect such isolators from metal deposition.

The support standoffs 170 may be distributed around the remainder of the coil to provide suitable support. In the illustrated embodiments the coils each have three hub members 504 distributed at 90 degree separations on the outer face of each coil. It should be appreciated that the number and spacing of the standoffs may be varied depending upon the particular application.

The coil 141 of the illustrated embodiments is each made of 2 by ⅛ inch knurled and bead-blasted tantalum ribbon formed into a single turn coil. However, other highly conductive materials and shapes may be utilized. For example, the thickness of the coil may be reduced to 1/16 inch. Also, hollow tubing may be utilized, particularly if water cooling is desired.

The appropriate RF generators and matching circuits are components well known to those skilled in the art. For example, an RF generator such as the ENI Genesis series which has the capability to frequency hunt for the best frequency match with the matching circuit and antenna is suitable. The frequency of the generator for generating the RF power to the coil is preferably 2 MHz but it is anticipated that the range can vary at other A.C. frequencies such as, for example, 1 MHz to 200 MHz and non-RF frequencies. These components may be controlled by the programmable controller 224 as well.

Figure 7:
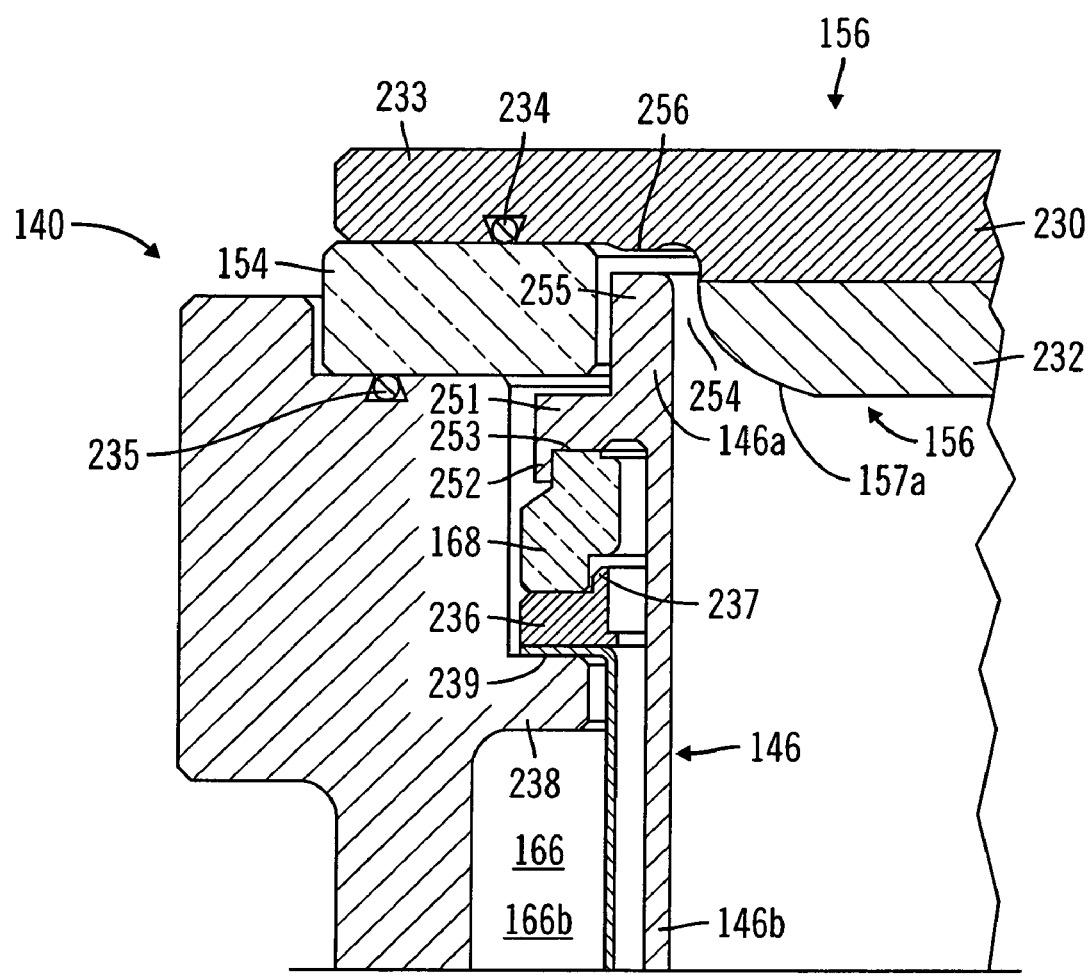
FIG. 7 is an enlarged view of a portion of the target and shields of FIG. 4.

As best seen in FIG. 7, the target 156 includes a backing plate 230 to which is soldered or diffusion bonded a target portion 232 of the metal to be deposited such as tantalum or copper. Suitable backing plate materials include aluminum, titanium, CuZn and CuCr. A flange 233 of the backing plate 230 rests on and is vacuum sealed through a polymeric target O-ring 234 to the target isolator 154, which is preferably composed of a ceramic such as alumina. The target isolator 154 rests on and is vacuum sealed through an adaptor O-ring 235 to the chamber 140, which in fact may be an aluminum adaptor sealed to the main chamber body.

A metal clamp ring 236 has on its inner radial side an upwardly extending annular rim 237. Bolts or other suitable fasteners fix the metal clamp ring 236 to an inwardly extending ledge 238 of the chamber 140 and capture a flange 239 of the chamber shield 166. Thereby, the chamber shield 166 is mechanically and electrically connected to the grounded chamber 140.

A flange 251 of the darkspace shield 146a freely rests on a shield isolator 168 and has a tab or rim 252 on its outside extending downwardly into an annular recess formed at the upper outer corner of the shield isolator 168. Thereby, the tab 252 centers the darkspace shield 146 with respect to the target 156 at the outer diameter of the shield isolator 168. The shield tab 252 is separated from the shield isolator 168 by a narrow gap which is sufficiently small to align the plasma dark spaces but sufficiently large to prevent jamming of the shield isolator 168, and the darkspace shield 146a rests on the shield isolator 168 in a sliding contact area 253 inside and above the tab 252.

A narrow channel 254 is formed between a head 255 of the darkspace shield 146 and the target 156. It has a width of about 2 mm to act as a plasma dark space. The inner shield 146 includes a downwardly extending cylindrical portion 146b. Similarly, the outer shield 166 has a cylindrical portion 166b connected on its upper end to the shield flange 239. The cylindrical portion 166b fits outside of and is thus wider than the shield cylindrical portion 146b.

Returning to the large view of FIG. 3, the cylindrical portion 146b of the chamber shield 146 continues downwardly to well below the top of the pedestal 162 supporting the wafer 158. The chamber shield 166 then continues radially inwardly in a bowl portion 146c and vertically upwardly in an innermost cylindrical portion 146d adjacent the pedestal 162.

The shields 146,166 are typically composed of stainless steel, and their inner sides may be bead blasted or otherwise roughened to promote adhesion of the material sputter deposited on them. At some point during prolonged sputtering, however, the deposited material builds up to a thickness that it is more likely to flake off, producing deleterious particles. Before this point is reached, the shields should be cleaned or replaced. However, the more expensive isolators 154, 168 do not need to be replaced in most maintenance cycles. The maintenance cycle is typically set to reduce flaking of the shields.

Referring again to FIG. 3, a gas source 314 supplies a sputtering working gas, typically the chemically inactive noble gas argon, to the chamber 140 through a mass flow controller 316. A vacuum pump system 320 connected to the chamber 140 through a wide pumping port 322 maintains the chamber at a low pressure. The computer-based controller 224 controls the reactor system including the flow controller 316 and the pump system 320.

To provide efficient sputtering, a magnetron 330 is positioned in back of the target 156. It has opposed magnets 332, 334 connected and supported by a magnetic yoke 336. The magnets create a magnetic field adjacent the magnetron 330 within the chamber 140. The magnetic field traps electrons and, for charge neutrality, the ion density also increases to form a high-density plasma region 338. The magnetron 330 is usually rotated about the center 340 of the target 156 by a motor-driven shaft 342 to achieve full coverage in sputtering of the target 156. To achieve a high-density plasma 338 of sufficient ionization density to allow sustained self-sputtering of copper, the power density delivered to the area adjacent the magnetron 330 is preferably made high. This can be achieved, as described by Fu in the above cited patents, by increasing the power level delivered from the DC power supply 200 and by reducing the area of magnetron 330, for example, in the shape of a triangle or a racetrack. In an alternative embodiment, a 60 degree triangular magnetron, may be rotated with its tip approximately coincident with the target center 340, to cover only about ⅙ of the target at any time. Coverage of ¼ or less is typical in a commercial reactor system capable of SIP sputtering.

When the argon is admitted into the chamber, the DC voltage difference between the target 156 and the chamber shield 146 ignites the argon into a plasma, and the positively charged argon ions are attracted to the negatively charged target 156. The ions strike the target 156 at a substantial energy and cause target atoms or atomic clusters to be sputtered from the target 156. Some of the target particles strike the wafer 158 and are thereby deposited on it, thereby forming a film of the target material. In reactive sputtering of a metallic nitride, nitrogen is additionally admitted into the chamber from a source 343, and it reacts with the sputtered metallic atoms to form a metallic nitride on the wafer 158.

In one embodiment, it is believed that good upper sidewall coverage and bottom corner coverage can be achieved in a multi-step process in which in one step, little or no RF power is applied to the coils. Thus, in one step, ionization of the sputtered target deposition material would occur primarily as a result of the self-ionization. Consequently, it is believed that good upper sidewall coverage may be achieved. In a second step and preferably in the same chamber, RF power may be applied to the coil 141 while low or no power is applied to the target. In this embodiment, little or no material would be sputtered from the target 156 while ionization of a precursor gas would occur primarily as a result of the RF energy inductively coupled by the coil 141. The ICP plasma may be directed to thin or eliminate bottom coverage by etching or resputtering to reduce barrier layer resistance at the bottom of the hole. In addition, the coil 141 may be sputtered to deposit protective material where thinning is not desired. In one embodiment, the pressure may be kept relatively low such that the plasma density is relatively low to reduce ionization of the sputtered deposition material from the coil. As a result, sputtered coil material can remain largely neutral so as to deposit primarily onto upper sidewalls to protect those portions from thinning. Once atoms of the underlying layer are detected by the detector 142 through the folded radiation path 143, resputtering may be terminated and the next layer deposited.

Since the illustrated reactor system 138 is capable of self-ionized sputtering, deposition material may be ionized not only as a result of the plasma maintained by the RF coil 141, but also by the sputtering of the target 156 itself. When it is desired to deposit a more conformal layer, it is believed that the combined SIP and ICP ionization processes provide sufficient ionized material for good bottom and bottom corner coverage. However, it is also believed that the lower ionization rate of the low pressure plasma provided by the RF coil 141 allows sufficient neutral sputtered material to remain un-ionized so as to be deposited on the upper sidewalls. Thus, it is believed that the combined sources of ionized deposition material can provide both good upper sidewall coverage as well as good bottom and bottom corner coverage. Again, bottom coverage may be thinned as needed by resputtering by applying an appropriate bias to the wafer.

In an alternative embodiment, it is believed that good upper sidewall coverage, bottom coverage and bottom corner coverage can be achieved in a multi-step process. In one step, little or no RF power is applied to the coils and ionization of the deposition material occurs as a result of the self-ionization, providing good upper sidewall coverage. In a second step and preferably in the same chamber, RF power may be applied to the coil 141. In addition, in one embodiment, the pressure may be raised substantially such that a high density plasma may be maintained. As a result, it is believed that good bottom and bottom corner coverage may be achieved in the second step. Resputtering may be terminated in the second step by the controller 224 when the plasma emissions detected by the detector 142 indicate that sufficient resputtering has occurred.

In one embodiment, rather than maintain the plasma at a relatively high pressure, such as 20–60 mTorr typical for high density IMP processes, the plasma is preferably maintained at a substantially lower pressure, such as 1 mTorr for deposition of tantalum nitride or 2.5 mTorr for deposition of tantalum, for example. However, pressures in the range of 0.1 to 40 mTorr may be appropriate, depending upon the application. As a consequence, it is believed that the ionization rate of sputtered metal within the reactor system 138 will be substantially lower than that of the typical high density IMP process.

Figure 8A:
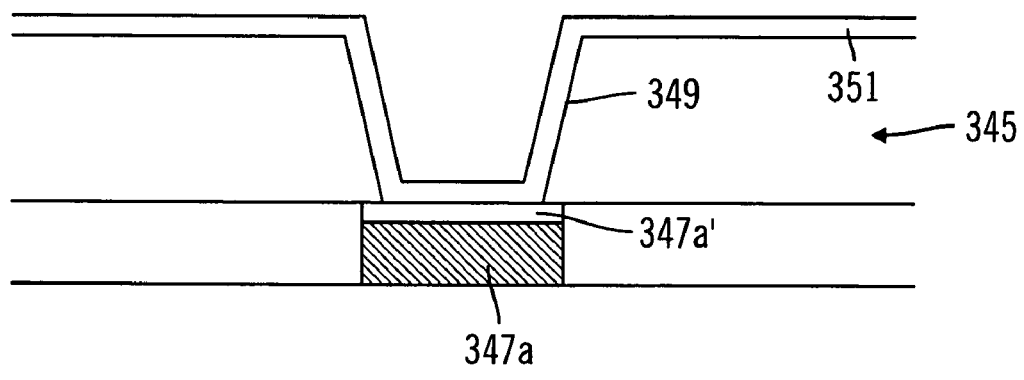
FIGS. 8A–8E are cross-sectional views of a via liner and via liner formation process according to one embodiment of the invention.
Figure 8B:
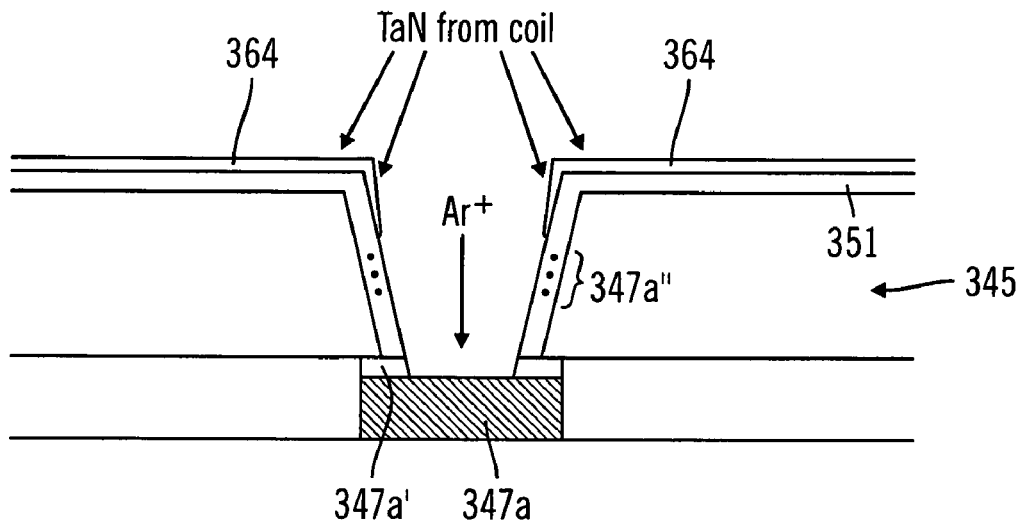
Figure 8C:
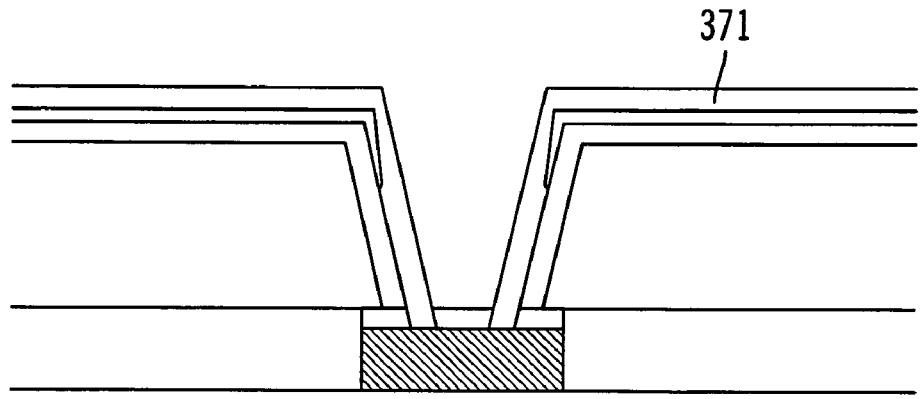
Figure 8D:
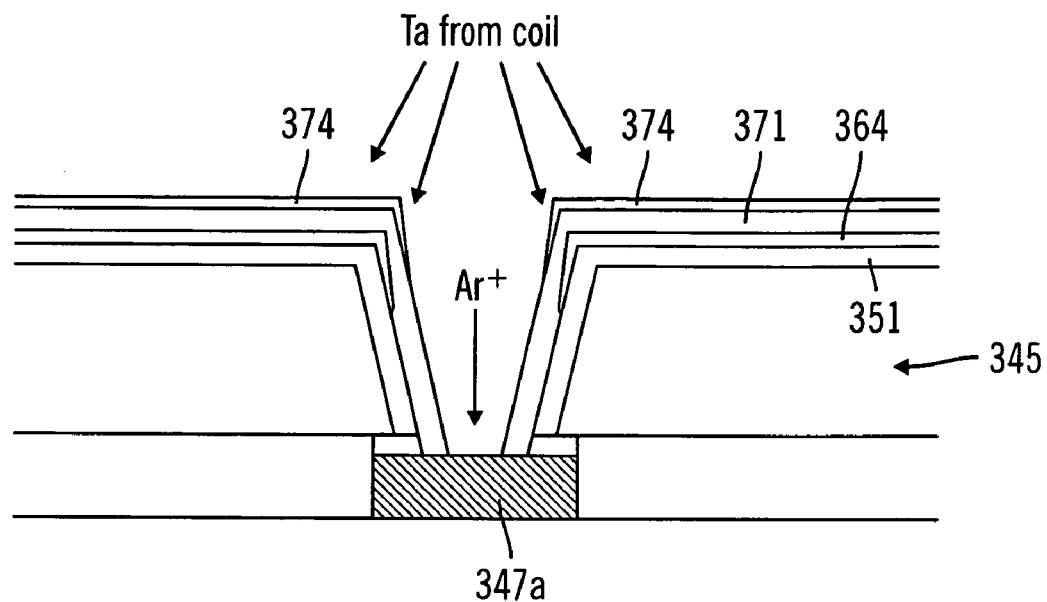
Figure 8E:
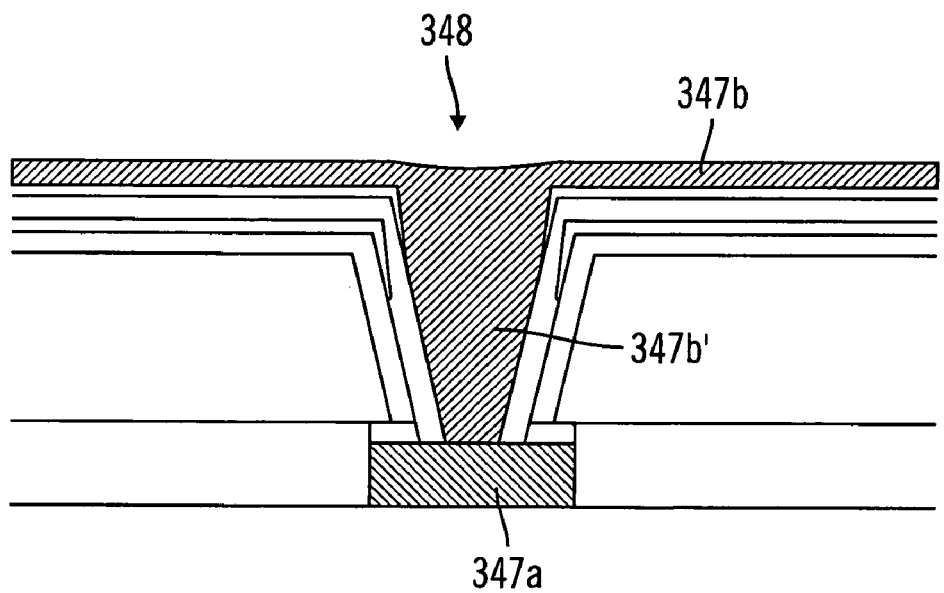

FIGS. 8A–E show sequential cross-sectional views of the formation of liner layers in accordance with one aspect of the present inventions. With reference to FIG. 8A, an interlayer dielectric 345 (e.g. silicon dioxide) is deposited over a first metal layer (e.g., a first copper layer 347a) of an interconnect 348 (FIG. 8E). A via 349 then is etched in the interlayer dielectric 345 to expose the first copper layer 347a. The first metal layer may be deposited using CVD, PVD, electroplating or other such well known metal deposition techniques, and it is connected, via contacts, through a dielectric layer, to devices formed in the underlying semiconductor wafer. If the first copper layer 347a is exposed to oxygen, such as when the wafer is moved from an etching chamber in which the oxide overlaying the first copper layer is etched to create apertures for creation of vias between the first copper layer and a second to be deposited metal layer, it can readily form an insulating/high resistance copper oxide layer 347a' thereon. Accordingly, to reduce the resistance of the copper interconnect 348, any copper oxide layer 347a' and any processing residue within the via 349 may be removed.

A barrier layer 351 may be deposited (e.g., within the sputtering chamber 140 of FIG. 3) over the interlayer dielectric 345 and over the exposed first copper layer 347a prior to removing the copper oxide layer 347a'. The barrier layer 351, preferably comprising tantalum, tantalum nitride, titanium nitride, tungsten or tungsten nitride prevents subsequently deposited copper layers from incorporating in and degrading the interlayer dielectric 345 (as previously described).

If, for example, the sputtering chamber 140 is configured for deposition of tantalum nitride layers, a tantalum target 156 is employed. Typically, both argon and nitrogen gas are admitted into the sputtering chamber 140 through gas inlets 360 while a power signal is applied to the target 156 via the DC power supply 200. Optionally, a power signal may also be applied to the coil 141 via the first RF generator power supply 206. During steady-state processing, nitrogen may react with the tantalum target 156 to form a nitride film on the tantalum target 156 so that tantalum nitride is sputtered therefrom. Additionally, non-nitrided tantalum atoms are also sputtered from the target, which atoms can combine with nitrogen to form tantalum nitride in flight or on a wafer (not shown) supported by the pedestal 162.

In operation, the deposition chamber 140 is maintained at a desired low vacuum level such as about $1\times10^{-8}$ Torr, prior to introduction of the process gas(es) into the chamber. To commence processing within the sputtering chamber 140, a mixture of argon and nitrogen gas is admitted into the sputtering chamber 140 via a gas inlet 360. After the gas stabilizes at a pressure of about 10–100 millitorr (preferably 10–60 millitorr, and more preferably 15–30 millitorr), DC power is applied to the tantalum target 156 via the DC power supply 200 (while the gas mixture continues to flow into the sputtering chamber 140 via the gas inlet 360 and is pumped therefrom via the pump system 320. The DC power applied to the target 156 causes the argon/nitrogen gas mixture to form an SIP plasma and to generate argon and nitrogen ions which are attracted to, and strike the target 156 causing target material (e.g., tantalum and tantalum nitride) to be ejected therefrom. The ejected target material travels to and deposits on the wafer 158 supported by the pedestal 162. In accordance with the SIP process, the plasma created by the unbalanced magnetron ionizes a portion of the sputtered tantalum and tantalum nitride. By adjusting the RF power signal applied to the substrate support pedestal 162, a negative bias can be created between the substrate support pedestal 162 and the plasma. The negative bias between the substrate support pedestal 162 and the plasma causes tantalum ions, tantalum nitride ions and argon ions to accelerate toward the pedestal 162 and any wafer supported thereon. Accordingly, both neutral and ionized tantalum nitride may be deposited on the wafer, providing good sidewall and upper sidewall coverage in accordance with SIP sputtering. In addition, particularly if RF power is applied to the ICP coil, the wafer may be sputter-etched by the argon ions at the same time the tantalum nitride material from the target 156 deposits on the wafer (i.e., simultaneous deposition/sputter-etching).

Figure 1:
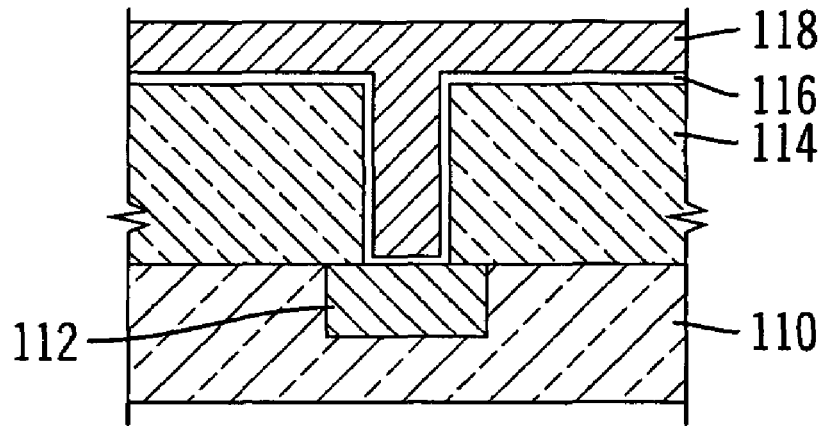
FIG. 1 is a cross-sectional view of a via filled with a metallization, which also covers the top of the dielectric, as practiced in the prior art.
Figure 2:
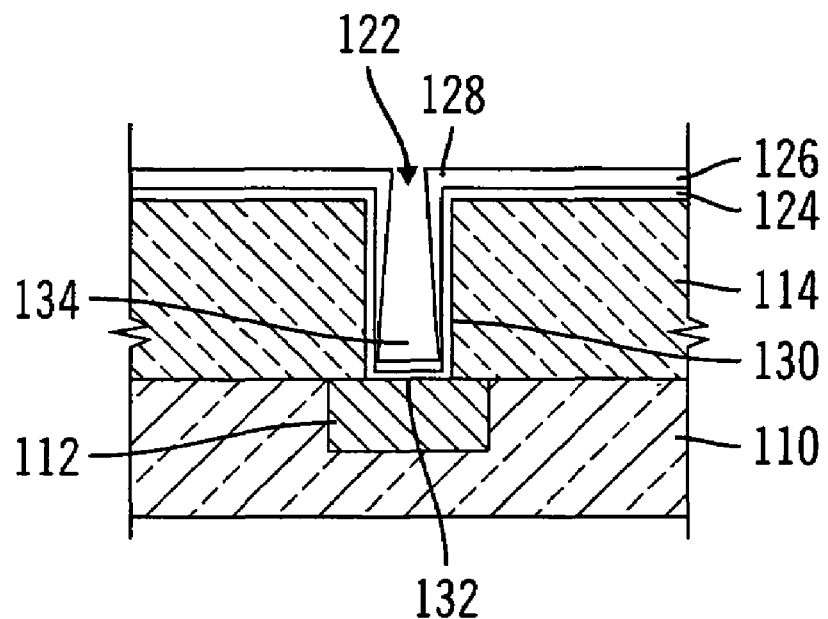
FIG. 2 is a cross-sectional view of a via during its filling with metallization, which overhangs and closes off the via hole.

Following deposition of the barrier layer 351, the portion of the barrier layer 351 at the bottom of the via 349, and the copper oxide layer 347a' (and any processing residue) thereunder, may be sputter-etched or resputtered via an argon plasma as shown in FIG. 8B, if thinning or elimination of the bottom is desired. The argon plasma is preferably generated in this step primarily by applying RF power to the ICP coil. Note that during sputter-etching within the sputtering chamber 140 (FIG. 2) in this embodiment, the power applied to the target 156 is preferably either removed or is reduced to a low level (e.g., 100 or 200 W) so as to inhibit or prevent significant deposition from the target 156. A low target power level, rather than no target power, mat provide a more uniform plasma and is presently preferred.

ICP argon ions are accelerated toward the barrier layer 351 via an electric field (e.g., the RF signal applied to the substrate support pedestal 162 via the second RF power supply 202 of FIG. 6 which causes a negative self bias to form on the pedestal), strike the barrier layer 351, and, due to momentum transfer, sputter the barrier layer material from the base of the via aperture and redistribute it along the portion of the barrier layer 351 that coats the sidewalls of the via 349. The argon ions are attracted to the substrate in a direction substantially perpendicular thereto. As a result, little sputtering of the via sidewall, but substantial sputtering of the via base, occurs. To facilitate resputtering, the bias applied to the pedestal and the wafer may be 400 watts, for example.

The particular values of the resputtering process parameters may vary depending upon the particular application. Thus, the endpoint detection system of the present invention may be used with a variety of resputtering and etch processes.

In the illustrated embodiment, the ICP coil 141 may be formed of liner material such as tantalum in the same manner as the target 156 and sputtered to deposit tantalum nitride onto the wafer while the via bottoms are resputtered. Because of the relatively low pressure during the resputtering process, the ionization rate of the deposition material sputtered from the coil 141 is relatively low. Hence, the sputtered material deposited onto the wafer is primarily neutral material.

In addition, the coil 141 is placed relatively low in the chamber, surrounding and adjacent to the wafer. Consequently, the trajectory of the material sputtered from the coil 141 tends to have a relatively small angle of incidence. Hence, the sputtered material from the coil 141 tends to deposit in a layer 364 on the upper surface of the wafer and around the openings of the holes or vias in the wafer rather than deep into the wafer holes. This deposited material from the coil 141 may be used to provide a degree of protection from resputtering so that the barrier layer is thinned by resputtering primarily at the bottom of the holes rather than on the sidewalls and around the hole openings where thinning of the barrier layer may not be desired.

The material sputtered from the coil 141 as well as the facing target 156 deposits not just on the substrate but on many if not all other exposed surfaces in the interior of the chamber. The inner and outer shields 146 and 166 protect the chamber walls 184 and the window 145 from the sputter deposition material.

Once the barrier layer 351 has been sputter-etched from the via base, the argon ions strike the copper oxide layer 347a', and the oxide layer is sputtered to redistribute the copper oxide layer material from the via base, some or all of the sputtered material being deposited along the portion of the barrier layer 351 that coats the sidewalls of the via 349. Copper atoms 347a", as well, coat the barrier layer 351 and 364 disposed on the sidewalls of the via 349. However, because the originally deposited barrier layer 351 along with that redistributed from the via base to via sidewall is a diffusion barrier to the copper atoms 347a", the copper atoms 347a" are substantially immobile within the barrier layer 351 and are inhibited from reaching the interlayer dielectric 345. The copper atoms 347a" which are deposited onto the sidewall, therefore, generally do not generate via-to-via leakage currents as they would were they redistributed onto an uncoated sidewall.

In addition to coating the barrier layer, trace quantities of sputtered copper atoms will become dispersed in the plasma. Prior to reaching the underlying layer, there should be no copper in the plasma or at least quantities which are below the trace quantities released when the copper layer is reached in the resputtering process. The copper atoms dispersed in the plasma will be electronically excited by the plasma. As the excited copper atoms decay, they will emit characteristic emission spectra which can be detected by the detector 142 via the folded radiation path 143. As previously mentioned, the folded radiation path conducts the plasma glow from the plasma generation area, around the shields 146 and 166, and to the optical view-port 145 and the detector 142 on the exterior of the chamber. Once the intensity of the copper emission spectra in the plasma glow becomes detectable by the detector or alternatively rises to a suitable level, the thinning of the barrier layer 351 by resputtering may be terminated.

Thereafter, a second liner layer 371 of a second material such as tantalum may be deposited (FIG. 8C) on the previous barrier layer 351 in the same chamber 140 or a similar chamber having both an SIP and ICP capabilities. A tantalum liner layer provides good adhesion between the underlying tantalum nitride barrier layer and a subsequently deposited metal interconnect layer of a conductor such as copper. The second liner layer 371 may be deposited in the same manner as the first liner layer 351. That is, the tantalum liner 371 may be deposited in a first SIP step in which the plasma is generated primarily by the target magnetron 330. However, nitrogen is not admitted so that tantalum rather than tantalum nitride is deposited. In accordance with SIP sputtering, good sidewall and upper sidewall coverage may be obtained. RF power to the ICP coil 141 may be reduced or eliminated, if desired.

Following deposition of the tantalum liner layer 371, the portion of the liner layer 371 at the bottom of the via 349 (and any processing residue thereunder), may be sputter-etched or resputtered via an argon plasma in the same manner as the bottom of the liner layer 351, as shown in FIG. 8D, if thinning or elimination of the bottom is desired. The argon plasma is preferably generated in this step primarily by applying RF power to the ICP coil. Again, note that during sputter-etching within the sputtering chamber 140 (FIG. 2), the power applied to the target 156 is preferably either removed or is reduced to a low level (e.g., 500 W) so as to inhibit or prevent significant deposition from the target 156 during thinning or elimination of the bottom coverage of the second liner layer 371. In addition, the coil 141 is preferably sputtered to deposit liner material 374 while the argon plasma resputters the layer bottom to protect the liner sidewalls and upper portions from being thinned substantially during the bottom portion resputtering.

Here again, once the liner layer 371 has been sputter-etched from the via base, the argon ions strike the copper layer such that trace quantities of sputtered copper atoms will become dispersed in the plasma. As the excited copper atoms decay, they will emit characteristic emission spectra which can be detected by the detector 142 via the folded radiation path 143. Once the intensity of the copper emission spectra in the plasma glow becomes detectable by the detector or alternatively rises to a suitable level, the thinning of the liner layer 371 by resputtering may be terminated.

In the above described embodiment, SIP deposition of target material on the sidewalls of the vias occurs primarily in one step and ICP resputtering of the via bottoms and ICP deposition of coil 141 material occurs primarily in a subsequent step. It is appreciated that deposition of both target material and coil material on the sidewalls of the via 349 can occur simultaneously, if desired. It is further appreciated that ICP sputter-etching of the deposited material at the bottom of the via 349 can occur simultaneously with the deposition of target and coil material on the sidewalls, if desired. Simultaneous deposition/sputter-etching may be performed with the chamber 140 of FIG. 3 by adjusting the power signals applied to the coil 141, the target 156 and the pedestal 162. Because the coil 141 can be used to maintain the plasma, the plasma can sputter a wafer with a low relative bias on the wafer (less than that needed to sustain the plasma). Once the sputtering threshold has been reached, for a particular wafer bias the ratio of the RF power applied to the wire coil 141 ("RF coil power") as compared to the DC power applied to the target 156 ("DC target power") affects the relationship between sputter-etching and deposition. For instance, the higher the RF:DC power ratio the more sputter-etching will occur due to increased ionization and subsequent increased ion bombardment flux to the wafer. Increasing the wafer bias will increase the energy of the incoming ions which will increase the sputtering yield and the etch rate. For example, increasing the voltage level of the RF signal applied to the pedestal 162 increases the energy of the ions incident on the wafer, while increasing the duty cycle of the RF signal applied to the pedestal 162 increases the number of incident ions.

Therefore, both the voltage level and the duty cycle of the wafer bias can be adjusted to control sputtering rate. In addition, keeping the DC target power low will decrease the amount of barrier material available for deposition. A DC target power of zero will result in sputter-etching only. A low DC target power coupled with a high RF coil power and wafer bias can result in simultaneous via sidewall deposition and via bottom sputtering. Accordingly, the process may be tailored for the material and geometries in question. For a typical 3:1 aspect ratio via on a 200 mm wafer, using tantalum or tantalum nitride as the barrier material, a DC target power of 500 W to 1 kW, at an RF coil power of 2 to 3 kW or greater, with a wafer bias of 250 W to 400 W or greater applied continuously (e.g., 100% duty cycle) can result in barrier deposition on the wafer sidewalls and removal of material from the via bottom. The lower the DC target power, the less material will be deposited on the sidewalls. The higher the DC target power, the more RF coil power and/or wafer bias power is needed to sputter the bottom of the via. A 2 kW RF coil power level on the coil 141 and a 250 W RF wafer power level with 100% duty cycle on the pedestal 162, for example may be used for simultaneous deposition/sputter-etching. It may be desirable to initially (e.g., for several seconds or more depending on the particular geometries/materials in question) apply no wafer bias during simultaneous deposition/sputter-etching to allow sufficient via sidewall coverage to prevent contamination of the sidewalls by material sputter-etched from the via bottom.

For instance, initially applying no wafer bias during simultaneous deposition/sputter-etching of the via 349 can facilitate formation of an initial barrier layer on the sidewalls of the interlayer dielectric 345 that inhibits sputtered copper atoms from contaminating the interlayer dielectric 345 during the remainder of the deposition/sputter-etching operation. Alternatively, deposition/sputter-etching may be performed sequentially within the same chamber or by depositing the barrier layer 351 within a first processing chamber and by sputter-etching the barrier layer 351 and copper oxide layer 347*a*' within a separate, second processing chamber (e.g., a sputter-etching chamber such as Applied Materials' Preclean II chamber).

Following deposition of the second liner layer 371 and thinning of the bottom coverage, a second metal layer 347*b* is deposited (FIG. 8E) to form the copper interconnect 348. The second copper layer 347b may be deposited either in a uniform layer or so as to form a copper plug 347b' as shown in FIG. 8E over the second liner layer 371 and over the portion of the first copper layer 347a exposed at the base of each via. Because the first and second copper layers 347a, 347b are in direct contact, rather than in contact through the barrier layer 351 or the second liner layer 371, the resistance of the copper interconnect 348 can be lower, as can via-to-via leakage currents.

If the interconnect is formed of a different conductor metal than the liner layer or layers, the interconnect layer may be deposited in a sputter chamber having a target of the different conductor metal. The sputter chamber may be an SIP type or an ICP type. The metal interconnect may be deposited by other methods in other types of chambers and apparatus including CVD and electrochemical plating.

Figure 9:
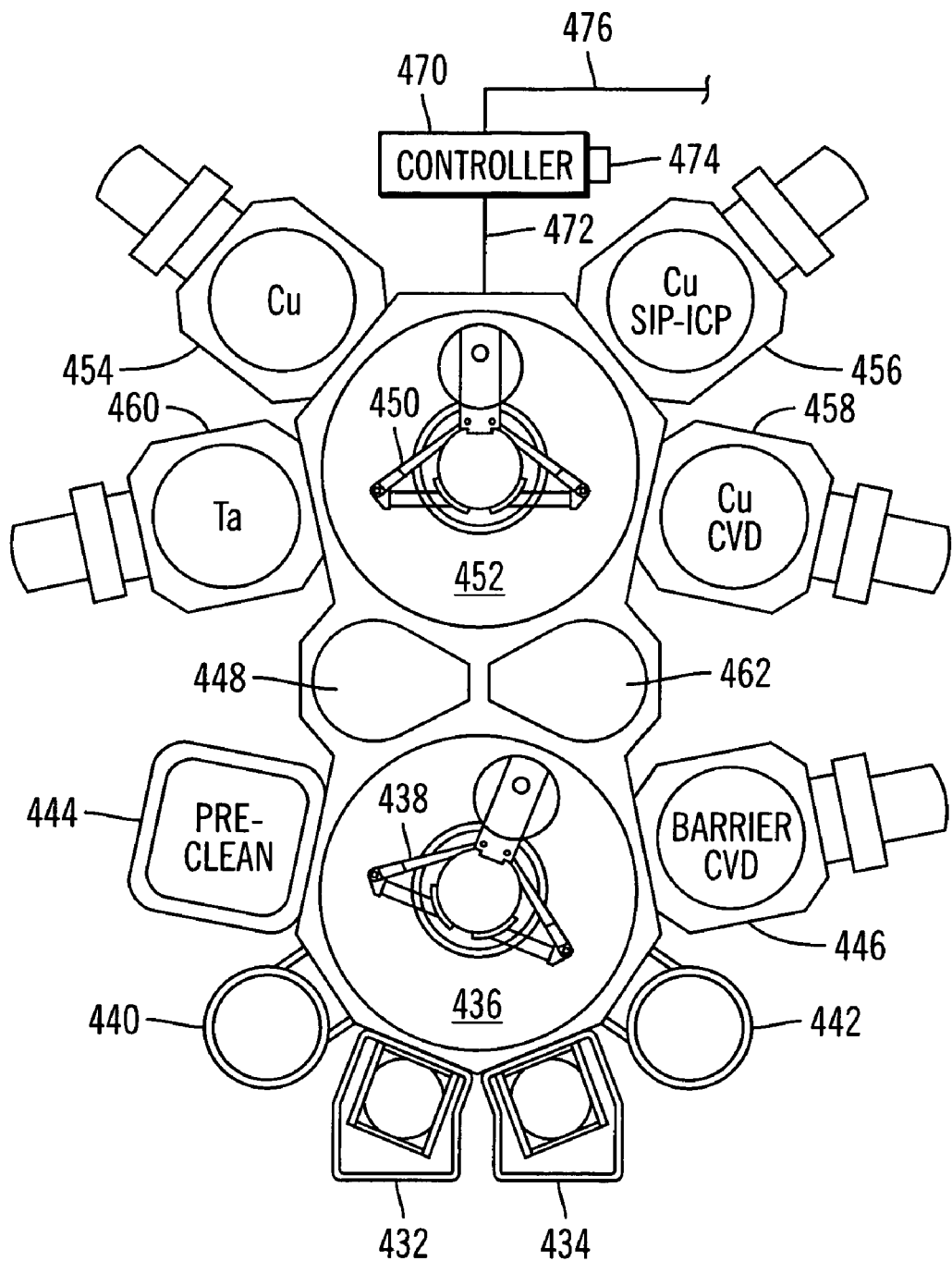
FIG. 9 is a schematic view of a integrated processing tool on which an embodiment of the invention may be practiced.

One embodiment of the present inventions includes an integrated process preferably practiced on an integrated multi-chamber tool, such as the Endura 5500 platform schematically illustrated in plan view in FIG. 9. The platform is functionally described by Tepman et al. in U.S. Pat. No. 5,186,718.

Wafers which previously have been etched with via holes or other structures in a dielectric layer are loaded into and out of the system through two independently operated load lock chambers 432, 434 configured to transfer wafers into and out of the system from wafer cassettes loaded into the respective load lock chambers. After a wafer cassette has been loaded into a load lock chamber 432, 434, the chamber is pumped to a moderately low pressure, for example, in the range of $10^{-3}$ to $10^{-4}$ Torr, and a slit valve between that load lock chamber and a first wafer transfer chamber 436 is opened. The pressure of the first wafer transfer chamber 436 is thereafter maintained at that low pressure.

A first robot 438 located in the first transfer chamber 436 transfers the wafer from the cassette to one of two degassing/orienting chambers 440, 442, and then to a first plasma pre-clean chamber 444, in which a hydrogen or argon plasma cleans the surface of the wafer. If a CVD barrier layer is being deposited, the first robot 438 then passes the wafer to a CVD barrier chamber 446. After the CVD barrier layer is deposited, the robot 438 passes the wafer into a pass through chamber 448, from whence a second robot 450 transfers it to a second transfer chamber 452. Slit valves separate the chambers 444, 446, 448 from the first transfer chamber 436 so as to isolate processing and pressure levels.

The second robot 450 selectively transfers wafers to and from reaction chambers arranged around the periphery. A first IMP sputter chamber 454 may be dedicated to the deposition of copper. An SIP-ICP sputter chamber 456 similar to the chamber 138 described above is dedicated to the deposition of the SIP-ICP copper nucleation layer. This chamber combines ICP deposition for bottom coverage and SIP deposition for sidewall coverage and reduced overhangs in either a one step or a multi-step process as discussed above. Also, at least part of the barrier layer (of, for example, Ta/TaN) is deposited by SIP sputtering and coil sputtering and ICP resputtering, and therefore a second SIP-ICP sputter chamber 460 is dedicated to sputtering a refractory metal, possibly in a reactive nitrogen plasma. The same SIP-ICP chamber 460 may be used for depositing the refractory metal and its nitride. A CVD chamber 458 is dedicated to the deposition of the copper seed layer and possibly used to complete the filling of the hole. Each of the chambers 454, 456, 458, 460 is selectively opened to the second transfer chambers 452 by slit valves. It is possible to use a different configuration. For example, an IMP chamber 454 may be replaced by a second CVD copper chamber, particularly if CVD is used to complete the hole filling.

After the low-pressure processing, the second robot 450 transfers the wafer to an intermediately placed thermal chamber 462, which may be a cool down chamber if the preceding processing was hot or may be a rapid thermal processing (RTP) chamber if annealing of the metallization is required. After thermal treatment, the first robot 438 withdraws the wafer and transfers it back to a cassette in one of the load lock chambers 432, 434. Of course, other configurations are possible with which the invention can be practiced depending on the steps of the integrated process.

The entire system is controlled by a computer-based controller 470 operating over a control bus 472 to be in communication with sub-controllers associated with each of the chambers. Process recipes are read into the controller 470 by recordable media 474, such as magnetic floppy disks or CD-ROMs, insertable into the controller 470, or over a communication link 476.

Many of the features of the apparatus and process of the inventions can be applied to sputtering not involving long-throw. Although the inventions are particularly useful at the present time for tantalum and tantalum nitride liner layer deposition and copper inter-level metallization, the different aspects of the invention may be applied to sputtering other materials and for other purposes.

It will, of course, be understood that modifications of the present invention, in its various aspects, will be apparent to those skilled in the art, some being apparent only after study, others being matters of routine mechanical and process design. Other embodiments are also possible, their specific designs depending upon the particular application. As such, the scope of the invention should not be limited by the particular embodiments herein described but should be defined only by the appended claims and equivalents thereof.

What is claimed is:

1. A method of depositing material onto a substrate having a substrate layer of material, comprising:
   generating a plasma within a chamber;
   sputtering metal material from a target within said chamber to deposit metal material onto said substrate layer;
   etching from said substrate within said chamber a portion of said metal material sputter deposited onto said substrate;
   monitoring through a folded radiation path within said chamber, radiation emitted by materials within said plasma; and
   terminating said etching in response to radiation monitored through said folded radiation path.

2. The method of claim 1 wherein said etching occurs while sputtering additional metal material onto said substrate.

3. The method of claim 2 wherein said sputtering additional metal material includes sputtering metal material from an RF coil.

4. The method of claim 3 wherein said coil sputtering includes biasing said coil to attract ions to sputter said coil.

5. The method of claim 3 wherein said generating includes applying RF power to said RF coil to generate ions and said etching includes biasing said substrate to attract said generated ions to said substrate.

6. The method of claim 1 wherein said monitoring includes detecting the composition of materials etched from said substrate as a function of the wavelengths of emitted radiation monitored while etching said substrate; and wherein said terminating includes terminating said etching in response to detection of an etched material composition.

7. The method of claim 1 further comprising blocking deposition onto a window of at least some material sputtered from said target using a wall positioned between said window and target and wherein said monitoring through a folded radiation path includes reflecting radiation emitted by said plasma around said wall to said window and monitoring the wavelengths of radiation transmitted through said window to a wavelength detector positioned outside said chamber window.

8. The method of claim 1 wherein said target sputtering includes rotating a magnetron about the back of the target, said magnetron having an area of no more than about ¼ of the area of the target and including an inner magnetic pole of one magnetic polarity surrounded by an outer magnetic pole of an opposite magnetic polarity, a magnetic flux of said outer pole being at least 50% larger than the magnetic flux of said inner pole.

9. A method of depositing material onto a substrate having a substrate layer, comprising:
   sputtering a target within a chamber to deposit target material onto said substrate within said chamber;
   ionizing at least a portion of said sputtered target material to form sputtered target material ions;
   biasing said substrate to attract said sputtered target material ions to deposit onto said substrate;
   sputtering a coil within said chamber to deposit coil material onto said substrate;
   energizing said coil to generate etchant ions in said chamber to resputter target material from said substrate;
   biasing said substrate to attract said etchant ions to resputter target material from said substrate;
   monitoring the wavelengths of radiation emitted by materials resputtered from said substrate while energizing said coil;
   detecting the composition of materials resputtered from said substrate as a function of the wavelengths of emitted radiation monitored while resputtering said substrate; and
   terminating said resputtering in response to detection of an etched material composition.

10. The method of claim 9 further comprising blocking deposition onto a window of at least some material sputtered from said target and said coil using a wall positioned between said window and said target and coil, and wherein said monitoring includes reflecting radiation emitted by said plasma through a folded radiation path around said wall to said window and monitoring the wavelengths of radiation transmitted through said window to a wavelength detector positioned outside said chamber window.

11. A method of depositing material onto a substrate having a conductor layer and an insulator overlying the conductor layer, comprising:
   sputtering a target within a chamber to deposit metal target material into holes in said insulation layer overlying said conductor layer of a substrate within said chamber;
   ionizing at least a portion of said sputtered target material to form sputtered target material ions;
   biasing said substrate to attract said sputtered target material ions to deposit target material into said holes of said substrate;
   energizing a coil within said chamber with RF energy to inductively couple RF energy into a plasma to generate etchant ions in said chamber to resputter material from said substrate;
   sputtering said coil within said chamber to deposit coil material onto said substrate while generating said etchant ions;
   blocking deposition onto a chamber window of at least some material sputtered from said target and said coil using a wall positioned between said window and said target and coil
   biasing said substrate to attract said etchant ions to resputter target material from the bottoms of holes of said substrate;
   monitoring the wavelengths of radiation emitted by materials resputtered from said substrate while sputtering said coil wherein said monitoring includes reflecting radiation emitted by said plasma through a folded radiation path around said wall to said window and monitoring the wavelengths of radiation transmitted through said window to a wavelength detector positioned outside said chamber window;
   using said detector, detecting the composition of materials resputtered from said substrate as a function of the wavelengths of emitted radiation monitored while resputtering said substrate; and
   terminating said resputtering in response to detection of conductor material of said conductor layer.

12. A process kit for a semiconductor sputter chamber having a window in a pressure wall, a detector disposed outside said window, a target and a workpiece support within said chamber and a plasma generation area between said workpiece support and said target, said kit comprising:
   a shield adapted to be positioned between said target and said support, said shield having an aperture facing said plasma generation area and adapted to receive radiation emitted by said plasma; and
   first and second reflective surfaces wherein said first reflective surface is adapted to be positioned to reflect radiation from said shield aperture to said second reflective surface and wherein said second reflective surface is adapted to be positioned to reflect radiation from said first reflective surface to said chamber window.

13. The kit of claim 12 further comprising a conduit adapted to be positioned between said shield aperture and said first reflective surface, said conduit having a plurality of internal reflective surfaces adapted to reflect radiation through said conduit.

14. The kit of claim 13 wherein said conduit has a first tubular portion having an opening facing said shield aperture and positioned to receive radiation from said shield aperture and said conduit further having a second tubular portion having an opening facing said first reflective surface and positioned to emit radiation to said first reflective surface wherein said first and second tubular portions are angled with respect to each other and said first and second tubular portions have a plurality of internal reflective surfaces adapted to reflect radiation from said first tubular portion opening to said second tubular portion opening.

15. A reactor for depositing material onto a substrate having a substrate layer of material, comprising:
   a vacuum chamber adapted to maintain a vacuum pressure within said chamber, said chamber having a pressure wall which includes a window;
   a substrate support disposed in said chamber and adapted to support said substrate;

a target surface disposed in said chamber and adapted to be sputtered to deposit metal material onto said substrate layer;

a coil disposed within said chamber and positioned to sputter coil material onto said substrate and to inductively couple energy to generate a plasma facing said substrate, said plasma emitting radiation wherein said chamber window is at least partially transparent to at least a portion of said plasma radiation;

a shield positioned to inhibit deposition of sputtered material onto said window; and a labyrinth disposed in said chamber between said plasma generation area and said window and adapted to conduct radiation from said plasma generation area to said window.

16. The reactor of claim 15 further comprising a magnetron disposed adjacent said target and having an area of no more than about ¼ of the area of the target and including an inner magnetic pole of one magnetic polarity surrounded by an outer magnetic pole of an opposite magnetic polarity, a magnetic flux of said outer pole being at least 50% larger than the magnetic flux of said inner pole.

17. A reactor for depositing material onto a substrate having a substrate layer of material, comprising:

a vacuum chamber adapted to maintain a vacuum pressure within said chamber, said chamber having a pressure wall which includes a window;

a substrate support disposed in said chamber and adapted to support said substrate;

a target surface disposed in said chamber and adapted to be sputtered to deposit metal material onto said substrate layer;

an etchant plasma generator disposed within said chamber and positioned to couple energy into the interior of said chamber to generate a plasma for resputtering said substrate, wherein said substrate support is adapted to bias said substrate to attract etchant plasma ions to resputter said substrate and wherein said plasma emits radiation and said chamber window is at least partially transparent to at least a portion of said plasma radiation;

a shield positioned to inhibit deposition of sputtered material onto said window; and a labyrinth disposed in said chamber between said plasma generation area and said window and adapted to conduct radiation from said plasma generation area to said window.

18. The reactor of claim 17 wherein said shield has an aperture and said labyrinth includes first and second reflective surfaces wherein said first reflective surface is positioned to reflect radiation from said shield aperture to said second reflective surface and wherein said second reflective surface is positioned to reflect radiation from said first reflective surface to said chamber window, and a conduit positioned between said shield aperture and said first reflective surface, said conduit having a plurality of internal reflective surfaces adapted to reflect radiation through said conduit.

19. The reactor of claim 18 wherein said conduit has a first tubular portion having an opening facing said shield aperture and positioned to receive radiation from said shield aperture and said conduit further having a second tubular portion having an opening facing said first reflective surface and positioned to emit radiation to said first reflective surface wherein said first and second tubular portions are angled with respect to each other and said first and second tubular portions have a plurality of internal reflective surfaces adapted to reflect radiation from said first tubular portion opening to said second tubular portion opening.

20. A system for depositing material onto a substrate having a substrate layer of material, comprising:

a chamber having a plasma generation area;

a substrate support disposed in said chamber and adapted to support said substrate;

a target disposed in said chamber and adapted to be sputtered to deposit metal material onto said substrate layer;

a first bias circuit coupled to said target and adapted to bias said target to sputter said target;

a plasma generator positioned to generate a plasma within said plasma generation area;

a second bias circuit adapted to bias said substrate to attract ions from said plasma to etch material from said substrate;

a monitor adapted to monitor radiation emitted by said plasma in said plasma generation area;

a labyrinth disposed in said chamber between said plasma generation area and said monitor and adapted to conduct radiation from said plasma generation area to said monitor; and a controller adapted to control said first and second bias circuits to etch material from said substrate after sputtering material onto said substrate; said controller further being adapted to be responsive to said monitor to terminate said etching in response to radiation monitored through said labyrinth.

21. The system of claim 20 wherein said plasma generator includes an RF coil disposed within said chamber around said plasma generation area and an RF power supply coupled to said RF coil.

22. The system of claim 21 further comprising a third bias circuit coupled to said RF coil to bias said coil to attract ions to sputter said RF coil to deposit coil material onto said substrate wherein said controller is adapted to control said third bias circuit to sputter coil material onto said substrate while etching material from said substrate, said controller further being adapted to terminate said coil sputtering when said etching is terminated.

23. The system of claim 20 further comprising a magnetron disposed adjacent said target and having an area of no more than about ¼ of the area of the target and including an inner magnetic pole of one magnetic polarity surrounded by an outer magnetic pole of an opposite magnetic polarity, a magnetic flux of said outer pole being at least 50% larger than the magnetic flux of said inner pole.

24. A process kit for a semiconductor sputter chamber having a window in a pressure wall, a detector disposed outside said window, a target having sputterable material and a workpiece support within said chamber and a plasma generation area between said workpiece support and said target, said kit comprising:

shield means adapted to be positioned between said target and said chamber window, for shielding said chamber window from material sputtered from said target, said shield means having aperture means facing said plasma generation area for receiving radiation emitted by said plasma; and radiation path means adapted to be positioned between said shield means and said chamber window, for reflecting radiation from said aperture means to said chamber window in a folded path.

25. A reactor system for depositing material onto a substrate having a substrate layer of material, comprising:

vacuum chamber means for maintaining a vacuum pressure, said chamber means having a pressure wall which includes a window;
means for generating a plasma within said chamber means;
target means for sputtering metal material within said chamber means to deposit metal material onto said substrate layer;
substrate biasing means for biasing said substrate to attract plasma ions to etch material from said substrate after metal material is sputtered onto said substrate;
monitoring means for monitoring radiation emitted by materials within said plasma, said monitoring means including radiation path means adapted to be positioned within said chamber between said plasma and said chamber means window, for reflecting radiation from said plasma to said chamber means window in a folded path; and
means for terminating said etching in response to radiation monitored through said radiation path means.

26. A system for depositing material onto a substrate having a substrate layer of material, comprising:
vacuum chamber means for maintaining a vacuum pressure, said chamber means having a pressure wall which includes a window;
substrate support means disposed in said chamber means for supporting said substrate;
target means for sputter depositing metal material onto said substrate layer;
plasma generator means positioned to generate a plasma within a plasma generation area within said chamber means;
substrate biasing means for biasing said substrate to attract ions from said plasma to etch material from said substrate;
monitor means for monitoring radiation emitted by said plasma in said plasma generation area, said monitoring means including a radiation detector and also including labyrinth means disposed in said chamber means between said plasma generation area and detector, for conducting radiation from said plasma generation area to said detector in a folded radiation path; and
controller means for controlling said target means, plasma generator means and bias means to etch material from said substrate after sputtering material onto said substrate; said controller means further being responsive to said monitoring means to terminate said etching in response to radiation monitored by said monitoring means through said labyrinth means.

* * * * *